(12) United States Patent
Perrow et al.

(10) Patent No.: US 8,361,126 B2
(45) Date of Patent: Jan. 29, 2013

(54) BONE PLATE SYSTEM

(75) Inventors: Scott J Perrow, Ishpeming, MI (US);
Brad S Fredin, Negaunee, MI (US);
Craig Filzetti, Marquette, MI (US);
Christian A Roose, Ishpeming, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 1129 days.

(21) Appl. No.: 12/199,321

(22) Filed: Aug. 27, 2008

(65) Prior Publication Data
US 2009/0062862 A1 Mar. 5, 2009

Related U.S. Application Data

(60) Provisional application No. 60/968,233, filed on Aug. 27, 2007, provisional application No. 60/947,873, filed on Jul. 3, 2007.

(51) Int. Cl.
*A61B 17/80* (2006.01)
(52) U.S. Cl. .......... 606/287; 606/289; 606/290
(58) Field of Classification Search ........... 606/70–71, 606/280–299
See application file for complete search history.

(56) References Cited

U.S. PATENT DOCUMENTS

| | | | |
|---|---|---|---|
| 434,503 A | 8/1890 | Corry | |
| 556,642 A | 3/1896 | Reessing | |
| 872,897 A | 12/1907 | Chapman et al. | |
| 951,800 A | 3/1910 | Center | |
| 1,084,680 A | 1/1914 | Wegener | |
| 1,087,797 A | 2/1914 | Lowe | |
| 1,385,780 A | 7/1921 | Dodds | |
| 1,409,157 A | 3/1922 | Dodds | |
| 1,756,239 A | 4/1930 | Chojnacki et al. | |
| 1,907,506 A | 5/1933 | Coburn | |
| 1,980,336 A | 11/1934 | Hoagland | |
| 2,248,054 A | 7/1941 | Becker | |
| 2,376,768 A | 5/1945 | Vasques | |
| 2,401,856 A | 6/1946 | Brock | |
| 2,580,821 A | 1/1952 | Nicola | |

(Continued)

FOREIGN PATENT DOCUMENTS

| DE | 251246 | 12/1911 |
|---|---|---|
| DE | 1949923 | 4/1971 |

(Continued)

OTHER PUBLICATIONS

Moftakhar, Roham, MD; Trost, Gregory, MD. Anterior Cervical Plates: A Historical Perspective. Neurosurgical Focus, vol. 16, No. 1. Jan. 2004. American Association of Neurological Surgeons; Charlottesville, VA, USA. 5 pages.

(Continued)

*Primary Examiner* — Thomas Barrett
*Assistant Examiner* — Matthew Lawson
(74) *Attorney, Agent, or Firm* — Fitch, Even, Tabin & Flannery, LLP

(57) ABSTRACT

Bone plate systems for surgical implants and bone repair are provided. The bone plate is multi-tiered for receiving bone anchors for securing a plurality of bones or bone fragments in a desired relationship. The plate members include throughbores for receiving a pivot base therein, with head ends of the bone anchors being secured within the pivot bases. The throughbores may permit and define a translation path for the pivot base and the bone anchor secured therein relative to the plate. The configuration of the pivot base and the throughbore facilitate pivoting and optional translation of the pivot base relative to the plate. With the bone anchor seated within the pivot base, an apparatus for inhibiting bone anchor back out is employed.

34 Claims, 18 Drawing Sheets

U.S. PATENT DOCUMENTS

| | | |
|---|---|---|
| 2,628,838 A | 2/1953 | Smalley |
| 2,780,223 A | 2/1957 | Haggland |
| 2,877,792 A | 3/1959 | Tybus |
| 3,100,516 A | 8/1963 | Naab |
| 3,244,170 A | 4/1966 | McElvenny |
| 3,426,364 A | 2/1969 | Lumb |
| 3,534,731 A | 10/1970 | Mueller |
| 3,596,656 A | 8/1971 | Kaute |
| 3,599,977 A | 8/1971 | Glass et al. |
| 3,659,595 A | 5/1972 | Haboush |
| 3,695,259 A | 10/1972 | Yost |
| 3,741,205 A | 6/1973 | Markolf et al. |
| 3,842,825 A | 10/1974 | Wagner |
| RE28,841 E | 6/1976 | Allgower et al. |
| 4,003,376 A | 1/1977 | McKay et al. |
| 4,029,091 A | 6/1977 | von Bezold et al. |
| 4,334,599 A | 6/1982 | Ritsema et al. |
| RE31,040 E | 9/1982 | Possis |
| 4,361,141 A | 11/1982 | Tanner |
| 4,388,921 A | 6/1983 | Sutter et al. |
| RE31,628 E | 7/1984 | Allgower et al. |
| 4,473,068 A | 9/1984 | Oh |
| 4,484,570 A | 11/1984 | Sutter et al. |
| 4,488,543 A | 12/1984 | Tornier |
| 4,493,317 A | 1/1985 | Klaue |
| 4,503,848 A | 3/1985 | Caspar et al. |
| 4,599,086 A | 7/1986 | Doty |
| 4,762,122 A | 8/1988 | Slocum |
| 4,771,767 A | 9/1988 | Steffee |
| 4,776,330 A | 10/1988 | Chapman et al. |
| 4,794,918 A | 1/1989 | Wolter |
| 4,890,845 A | 1/1990 | Gatewood |
| 4,892,545 A | 1/1990 | Day et al. |
| 4,904,261 A | 2/1990 | Dove et al. |
| 4,905,679 A | 3/1990 | Morgan |
| 4,943,292 A | 7/1990 | Foux |
| 4,955,908 A | 9/1990 | Frey et al. |
| 4,957,497 A | 9/1990 | Hoogland et al. |
| 4,964,403 A | 10/1990 | Karas et al. |
| 5,002,544 A | 3/1991 | Klaue et al. |
| 5,041,113 A | 8/1991 | Biedermann et al. |
| 5,041,114 A | 8/1991 | Chapman et al. |
| 5,053,036 A | 10/1991 | Perren et al. |
| 5,057,111 A | 10/1991 | Park |
| 5,085,660 A | 2/1992 | Lin |
| 5,092,320 A | 3/1992 | Maurer |
| 5,108,395 A | 4/1992 | Laurain |
| 5,113,685 A | 5/1992 | Asher et al. |
| 5,127,912 A | 7/1992 | Ray et al. |
| 5,127,914 A | 7/1992 | Calderale et al. |
| 5,129,899 A | 7/1992 | Small et al. |
| 5,129,903 A | 7/1992 | Luhr et al. |
| 5,139,498 A | 8/1992 | Astudillo Ley |
| 5,147,360 A | 9/1992 | Dubousset |
| 5,147,361 A | 9/1992 | Ojima et al. |
| 5,151,103 A | 9/1992 | Tepic et al. |
| 5,180,381 A | 1/1993 | Aust et al. |
| 5,190,544 A | 3/1993 | Chapman et al. |
| 5,234,431 A | 8/1993 | Keller |
| 5,261,910 A | 11/1993 | Warden et al. |
| 5,269,784 A | 12/1993 | Mast |
| 5,275,601 A | 1/1994 | Gogolewski et al. |
| 5,304,179 A | 4/1994 | Wagner |
| 5,324,290 A | 6/1994 | Zdeblick et al. |
| 5,326,206 A | 7/1994 | Moore |
| 5,330,535 A | 7/1994 | Moser et al. |
| 5,344,421 A | 9/1994 | Crook |
| 5,346,492 A | 9/1994 | Morgan |
| 5,364,399 A | 11/1994 | Lowery et al. |
| 5,380,323 A | 1/1995 | Howland |
| 5,380,327 A | 1/1995 | Eggers et al. |
| 5,382,248 A | 1/1995 | Jacobson et al. |
| 5,397,363 A | 3/1995 | Gelbard |
| 5,397,364 A | 3/1995 | Kozak et al. |
| 5,415,661 A | 5/1995 | Holmes |
| 5,423,826 A | 6/1995 | Coates et al. |
| 5,454,769 A | 10/1995 | Chen |
| 5,458,641 A | 10/1995 | Ramirez Jimenez |
| 5,468,242 A | 11/1995 | Reisberg |
| 5,478,342 A | 12/1995 | Kohrs |
| 5,486,176 A | 1/1996 | Hildebrand et al. |
| 5,501,684 A | 3/1996 | Schlapfer et al. |
| 5,520,690 A | 5/1996 | Errico et al. |
| 5,520,696 A | 5/1996 | Wenstrom, Jr. |
| 5,522,899 A | 6/1996 | Michelson |
| 5,527,311 A | 6/1996 | Procter et al. |
| 5,531,746 A | 7/1996 | Errico et al. |
| 5,534,027 A | 7/1996 | Hodorek |
| 5,534,032 A | 7/1996 | Hodorek |
| 5,549,612 A | 8/1996 | Yapp et al. |
| 5,569,247 A | 10/1996 | Morrison |
| 5,571,109 A | 11/1996 | Bertagnoli |
| 5,578,034 A | 11/1996 | Estes |
| 5,601,553 A | 2/1997 | Trebing et al. |
| 5,603,713 A | 2/1997 | Aust et al. |
| 5,607,426 A | 3/1997 | Ralph et al. |
| 5,607,428 A | 3/1997 | Lin |
| 5,616,144 A | 4/1997 | Yapp et al. |
| 5,620,443 A | 4/1997 | Gertzbein et al. |
| 5,626,449 A | 5/1997 | McKinlay |
| 5,643,265 A | 7/1997 | Errico et al. |
| 5,647,872 A | 7/1997 | Gilbert et al. |
| 5,651,651 A | 7/1997 | Spencer |
| 5,653,708 A | 8/1997 | Howland |
| 5,667,513 A | 9/1997 | Torrie et al. |
| 5,676,666 A | 10/1997 | Oxland et al. |
| 5,676,703 A | 10/1997 | Gelbard |
| 5,681,311 A | 10/1997 | Foley et al. |
| 5,681,312 A | 10/1997 | Yuan et al. |
| 5,683,465 A | 11/1997 | Shinn et al. |
| 5,690,631 A | 11/1997 | Duncan et al. |
| 5,704,936 A | 1/1998 | Mazel |
| 5,707,372 A | 1/1998 | Errico et al. |
| 5,709,686 A | 1/1998 | Talos et al. |
| 5,713,900 A | 2/1998 | Benzel et al. |
| 5,725,588 A | 3/1998 | Errico et al. |
| 5,731,275 A | 3/1998 | Prevost et al. |
| 5,735,850 A | 4/1998 | Baumgartner et al. |
| 5,735,853 A | 4/1998 | Olerud |
| 5,735,899 A | 4/1998 | Schwartz et al. |
| 5,741,258 A | 4/1998 | Klaue et al. |
| 5,766,176 A | 6/1998 | Duncan |
| 5,766,254 A | 6/1998 | Gelbard |
| 5,797,912 A | 8/1998 | Runciman et al. |
| 5,800,433 A | 9/1998 | Benzel et al. |
| 5,807,396 A | 9/1998 | Raveh |
| 5,810,823 A | 9/1998 | Klaue et al. |
| 5,814,048 A | 9/1998 | Morgan |
| 5,827,285 A | 10/1998 | Bramlet |
| 5,840,078 A | 11/1998 | Yerys |
| 5,843,082 A | 12/1998 | Yuan et al. |
| 5,876,402 A | 3/1999 | Errico et al. |
| 5,879,389 A | 3/1999 | Koshino |
| 5,888,221 A | 3/1999 | Gelbard |
| 5,904,683 A | 5/1999 | Pohndorf et al. |
| 5,916,200 A | 6/1999 | Eppley et al. |
| 5,951,557 A | 9/1999 | Luter |
| 5,951,558 A | 9/1999 | Fiz |
| 5,954,722 A | 9/1999 | Bono |
| 5,964,762 A | 10/1999 | Biedermann et al. |
| 5,976,141 A | 11/1999 | Haag et al. |
| 5,980,540 A | 11/1999 | Bruce |
| 5,984,924 A | 11/1999 | Asher et al. |
| 6,017,345 A | 1/2000 | Richelsoph |
| 6,022,350 A | 2/2000 | Ganem |
| 6,030,389 A | 2/2000 | Wagner et al. |
| 6,036,693 A | 3/2000 | Yuan et al. |
| 6,039,740 A | 3/2000 | Olerud |
| 6,090,111 A | 7/2000 | Nichols |
| 6,106,557 A | 8/2000 | Robioneck et al. |
| 6,117,173 A | 9/2000 | Taddia et al. |
| 6,129,730 A | 10/2000 | Bono et al. |
| 6,132,434 A | 10/2000 | Sherman et al. |
| 6,139,550 A | 10/2000 | Michelson |
| 6,152,927 A | 11/2000 | Farris et al. |
| 6,159,213 A | 12/2000 | Rogozinski |
| 6,183,476 B1 | 2/2001 | Gerhardt et al. |

| Patent No. | Date | Name |
|---|---|---|
| 6,189,422 B1 | 2/2001 | Stihl |
| 6,193,720 B1 | 2/2001 | Yuan |
| 6,193,721 B1 | 2/2001 | Michelson |
| 6,206,881 B1 | 3/2001 | Frigg et al. |
| 6,206,882 B1 | 3/2001 | Cohen |
| 6,214,005 B1 | 4/2001 | Benzel et al. |
| 6,224,602 B1 | 5/2001 | Hayes |
| 6,228,085 B1 | 5/2001 | Theken et al. |
| 6,235,032 B1 | 5/2001 | Link |
| 6,235,033 B1 | 5/2001 | Brace et al. |
| 6,235,034 B1 | 5/2001 | Bray |
| 6,241,731 B1 | 6/2001 | Fiz |
| 6,254,603 B1 | 7/2001 | Gertzbein et al. |
| 6,257,593 B1 | 7/2001 | White |
| 6,258,089 B1 | 7/2001 | Campbell et al. |
| 6,261,042 B1 | 7/2001 | Pratt |
| 6,261,291 B1 | 7/2001 | Talaber et al. |
| 6,273,889 B1 | 8/2001 | Richelsoph |
| 6,280,445 B1 | 8/2001 | Morrison et al. |
| 6,290,703 B1 | 9/2001 | Ganem |
| 6,293,949 B1 | 9/2001 | Justis et al. |
| D449,692 S | 10/2001 | Michelson |
| 6,306,136 B1 | 10/2001 | Baccelli |
| 6,306,139 B1 | 10/2001 | Fuentes |
| 6,315,779 B1 | 11/2001 | Morrison et al. |
| 6,322,562 B1 | 11/2001 | Wolter |
| 6,328,738 B1 | 12/2001 | Suddaby |
| 6,331,179 B1 | 12/2001 | Freid et al. |
| 6,332,887 B1 | 12/2001 | Knox |
| 6,342,055 B1 | 1/2002 | Eisermann et al. |
| 6,342,057 B1 | 1/2002 | Brace et al. |
| 6,361,537 B1 | 3/2002 | Anderson |
| 6,364,880 B1 | 4/2002 | Michelson |
| 6,379,364 B1 | 4/2002 | Brace et al. |
| 6,381,806 B1 | 5/2002 | Stanesic et al. |
| 6,383,186 B1 | 5/2002 | Michelson |
| 6,398,783 B1 | 6/2002 | Michelson |
| 6,402,206 B1 | 6/2002 | Simmons et al. |
| 6,402,755 B1 | 6/2002 | Pisharodi |
| 6,402,756 B1 | 6/2002 | Ralph et al. |
| 6,402,759 B1 | 6/2002 | Strong et al. |
| 6,406,478 B1 | 6/2002 | Kuo |
| 6,413,259 B1 | 7/2002 | Lyons et al. |
| 6,416,528 B1 | 7/2002 | Michelson |
| 6,423,068 B1 | 7/2002 | Reisberg et al. |
| 6,428,542 B1 | 8/2002 | Michelson |
| 6,454,769 B2 | 9/2002 | Wagner et al. |
| 6,454,771 B1 | 9/2002 | Michelson |
| 6,458,133 B1 | 10/2002 | Lin |
| 6,471,704 B2 | 10/2002 | Gertzbein et al. |
| 6,478,797 B1 | 11/2002 | Paul |
| 6,503,250 B2 | 1/2003 | Paul |
| 6,527,776 B1 | 3/2003 | Michelson |
| 6,533,786 B1 | 3/2003 | Needham et al. |
| 6,572,619 B2 | 6/2003 | Santilli |
| 6,575,975 B2 | 6/2003 | Brace et al. |
| 6,579,290 B1 | 6/2003 | Hardcastle et al. |
| 6,585,769 B1 | 7/2003 | Muhanna et al. |
| 6,592,586 B1 | 7/2003 | Michelson |
| 6,595,993 B2 | 7/2003 | Donno |
| 6,599,290 B2 | 7/2003 | Bailey |
| 6,602,255 B1 | 8/2003 | Campbell et al. |
| 6,602,256 B1 | 8/2003 | Hayes |
| 6,602,257 B1 | 8/2003 | Thramann |
| 6,605,090 B1 | 8/2003 | Trieu et al. |
| 6,613,053 B1 | 9/2003 | Collins et al. |
| 6,613,728 B1 | 9/2003 | Sirianni et al. |
| 6,616,666 B1 | 9/2003 | Michelson |
| 6,620,163 B1 | 9/2003 | Michelson |
| 6,623,486 B1 | 9/2003 | Weaver et al. |
| 6,626,907 B2 | 9/2003 | Campbell et al. |
| 6,627,590 B1 | 9/2003 | Sherry et al. |
| 6,652,525 B1 | 11/2003 | Assaker et al. |
| 6,663,632 B1 | 12/2003 | Frigg |
| 6,669,700 B1 | 12/2003 | Farris et al. |
| 6,692,503 B2 | 2/2004 | Foley et al. |
| 6,695,846 B2 | 2/2004 | Richelsoph et al. |
| 6,755,833 B1 | 6/2004 | Paul et al. |
| D501,231 S | 1/2005 | Rom |
| 6,860,883 B2 | 3/2005 | Janowski et al. |
| 6,890,334 B2 | 5/2005 | Brace et al. |
| 6,890,335 B2 | 5/2005 | Grabowski et al. |
| 6,916,320 B2 | 7/2005 | Michelson |
| 6,964,664 B2 | 11/2005 | Freid et al. |
| 6,966,735 B1 | 11/2005 | Yamazaki |
| 7,048,739 B2 | 5/2006 | Konieczynski et al. |
| 7,074,221 B2 | 7/2006 | Michelson |
| 7,273,481 B2 | 9/2007 | Lombardo et al. |
| 7,410,496 B2 | 8/2008 | Derouet |
| 7,452,370 B2 | 11/2008 | Anderson |
| 7,476,239 B2 | 1/2009 | Jackson |
| 7,618,443 B2 | 11/2009 | Abdou |
| 7,635,366 B2 | 12/2009 | Abdou |
| 7,662,175 B2 | 2/2010 | Jackson |
| 7,666,185 B2 | 2/2010 | Ryan et al. |
| 7,682,379 B2 | 3/2010 | Mathieu et al. |
| 7,766,915 B2 | 8/2010 | Jackson |
| 7,780,706 B2 | 8/2010 | Marino et al. |
| 7,794,482 B2 | 9/2010 | Mathieu et al. |
| 7,854,752 B2 | 12/2010 | Colleran et al. |
| 7,857,836 B2 | 12/2010 | Huebner et al. |
| 7,862,591 B2 | 1/2011 | Dewey et al. |
| 7,875,065 B2 | 1/2011 | Jackson |
| 7,887,569 B2 | 2/2011 | Frigg |
| 7,901,437 B2 | 3/2011 | Jackson |
| 7,909,852 B2 | 3/2011 | Boomer et al. |
| 7,927,359 B2 | 4/2011 | Trautwein et al. |
| 7,935,126 B2 | 5/2011 | Orbay et al. |
| 7,942,909 B2 | 5/2011 | Hammill, Sr. et al. |
| 7,942,910 B2 | 5/2011 | Doubler et al. |
| 7,942,911 B2 | 5/2011 | Doubler et al. |
| 7,947,065 B2 | 5/2011 | Hammill, Sr. et al. |
| 7,951,170 B2 | 5/2011 | Jackson |
| 7,951,173 B2 | 5/2011 | Hammill, Sr. et al. |
| 7,951,179 B2 | 5/2011 | Matityahu |
| 7,967,850 B2 | 6/2011 | Jackson |
| 8,012,177 B2 | 9/2011 | Jackson |
| 8,025,681 B2 | 9/2011 | Colleran et al. |
| 2001/0014807 A1 | 8/2001 | Wagner et al. |
| 2001/0021851 A1 | 9/2001 | Eberlein et al. |
| 2001/0037112 A1 | 11/2001 | Brace et al. |
| 2001/0041894 A1 | 11/2001 | Campbell et al. |
| 2001/0047172 A1 | 11/2001 | Foley et al. |
| 2001/0047174 A1 | 11/2001 | Donno et al. |
| 2002/0013586 A1 | 1/2002 | Justis et al. |
| 2002/0016595 A1 | 2/2002 | Michelson |
| 2002/0022843 A1 | 2/2002 | Michelson |
| 2002/0029040 A1 | 3/2002 | Morrison et al. |
| 2002/0045896 A1 | 4/2002 | Michelson |
| 2002/0045898 A1 | 4/2002 | Freid et al. |
| 2002/0045899 A1 | 4/2002 | Errico et al. |
| 2002/0049444 A1 | 4/2002 | Knox |
| 2002/0058939 A1 | 5/2002 | Wagner et al. |
| 2002/0065517 A1 | 5/2002 | Paul |
| 2002/0068938 A1 | 6/2002 | Jackson |
| 2002/0077630 A1 | 6/2002 | Lin |
| 2002/0111630 A1 | 8/2002 | Ralph et al. |
| 2002/0120268 A1 | 8/2002 | Berger |
| 2002/0120271 A1 | 8/2002 | Dixon et al. |
| 2002/0120272 A1 | 8/2002 | Yuan et al. |
| 2002/0120273 A1 | 8/2002 | Needham et al. |
| 2002/0128654 A1 | 9/2002 | Steger et al. |
| 2002/0128655 A1 | 9/2002 | Michelson |
| 2002/0151893 A1 | 10/2002 | Santilli |
| 2002/0151899 A1 | 10/2002 | Bailey et al. |
| 2002/0151900 A1 | 10/2002 | Glascott |
| 2002/0156474 A1 | 10/2002 | Wack et al. |
| 2002/0161370 A1 | 10/2002 | Frigg et al. |
| 2002/0173790 A1 | 11/2002 | Chang et al. |
| 2002/0183747 A1 | 12/2002 | Jao et al. |
| 2002/0183754 A1 | 12/2002 | Michelson |
| 2002/0183755 A1 | 12/2002 | Michelson |
| 2002/0183756 A1 | 12/2002 | Michelson |
| 2002/0183757 A1 | 12/2002 | Michelson |
| 2002/0188296 A1 | 12/2002 | Michelson |
| 2003/0023242 A1 | 1/2003 | Harrington, Jr. |
| 2003/0060828 A1 | 3/2003 | Michelson |
| 2003/0078583 A1 | 4/2003 | Biedermann et al. |

| | | | | | | |
|---|---|---|---|---|---|---|
| 2003/0093082 | A1 | 5/2003 | Campbell et al. | EP | 0 999 796 B1 | 5/2000 |
| 2003/0105462 | A1 | 6/2003 | Haider | EP | 0999796 | 5/2000 |
| 2003/0130661 | A1 | 7/2003 | Osman | EP | 0 767 631 B1 | 12/2000 |
| 2003/0149434 | A1 | 8/2003 | Paul | EP | 1 106 144 A1 | 6/2001 |
| 2003/0153920 | A1 | 8/2003 | Ralph et al. | EP | 1106114 A1 | 6/2001 |
| 2003/0181912 | A1 | 9/2003 | Michelson | EP | 1169971 A2 | 1/2002 |
| 2003/0187440 | A1 | 10/2003 | Richelsoph et al. | EP | 1 185 210 | 3/2002 |
| 2003/0187441 | A1 | 10/2003 | Bolger et al. | EP | 1 220 645 B1 | 7/2002 |
| 2003/0187442 | A1 | 10/2003 | Richelsoph et al. | EP | 1 306 058 A2 | 7/2002 |
| 2003/0187509 | A1 | 10/2003 | Lemole, Jr. | EP | 1285632 | 2/2003 |
| 2003/0191471 | A1 | 10/2003 | Michelson | EP | 0 874 595 B1 | 3/2003 |
| 2003/0191472 | A1 | 10/2003 | Michelson | EP | 0 809 971 B1 | 4/2003 |
| 2003/0225409 | A1 | 12/2003 | Freid et al. | EP | 0876128 | 5/2003 |
| 2004/0019353 | A1 | 1/2004 | Fried et al. | EP | 1336383 | 8/2003 |
| 2004/0030338 | A1 | 2/2004 | Paul | EP | 1340468 A2 | 9/2003 |
| 2004/0087951 | A1 | 5/2004 | Khalili | EP | 1346697 | 9/2003 |
| 2004/0092938 | A1 | 5/2004 | Carli | EP | 1364623 | 11/2003 |
| 2004/0097934 | A1 | 5/2004 | Farris et al. | FR | 2435243 | 4/1980 |
| 2004/0097935 | A1 | 5/2004 | Richelsoph et al. | FR | 2519857 | 7/1983 |
| 2004/0097950 | A1 | 5/2004 | Foley et al. | FR | 2556583 | 6/1985 |
| 2004/0122426 | A1 | 6/2004 | Michelson | FR | 2726461 | 5/1996 |
| 2004/0127896 | A1 | 7/2004 | Lombardo et al. | FR | 2740321 | 4/1997 |
| 2004/0127897 | A1 | 7/2004 | Freid et al. | FR | 2794963 | 12/2000 |
| 2004/0127899 | A1 | 7/2004 | Konieczynski et al. | FR | 2810532 | 12/2001 |
| 2004/0127900 | A1 | 7/2004 | Konieczynski et al. | JP | 599640 A1 | 6/1994 |
| 2004/0158246 | A1 | 8/2004 | Assaker et al. | SU | 1424824 | 9/1988 |
| 2004/0186482 | A1 | 9/2004 | Kolb et al. | WO | 8803781 | 6/1988 |
| 2004/0204710 | A1 | 10/2004 | Patel et al. | WO | WO 88/03781 | 6/1988 |
| 2004/0204716 | A1 | 10/2004 | Fanger et al. | WO | WO 91/03994 | 4/1991 |
| 2004/0204717 | A1 | 10/2004 | Fanger et al. | WO | 9417744 A1 | 8/1994 |
| 2004/0220570 | A1* | 11/2004 | Frigg ............... 606/69 | WO | WO 95/25474 | 9/1995 |
| 2004/0220571 | A1 | 11/2004 | Assaker et al. | WO | WO 95/31941 | 11/1995 |
| 2004/0236334 | A1 | 11/2004 | Michelson | WO | WO 96/00530 | 1/1996 |
| 2005/0033298 | A1* | 2/2005 | Hawkes et al. ............... 606/61 | WO | 9605778 A1 | 2/1996 |
| 2005/0038436 | A1 | 2/2005 | Michelson | WO | WO 96/08206 | 3/1996 |
| 2005/0049593 | A1 | 3/2005 | Duong et al. | WO | 9632071 A1 | 10/1996 |
| 2005/0192577 | A1 | 9/2005 | Mosca et al. | WO | WO 96/29948 | 10/1996 |
| 2005/0234456 | A1 | 10/2005 | Malandain | WO | 9639975 | 12/1996 |
| 2006/0079900 | A1 | 4/2006 | Mathieu et al. | WO | WO 97/22306 | 6/1997 |
| 2006/0106387 | A1 | 5/2006 | Fanger et al. | WO | 9834553 A1 | 8/1998 |
| 2006/0122602 | A1 | 6/2006 | Konieczynski et al. | WO | 9834556 A1 | 8/1998 |
| 2006/0122604 | A1 | 6/2006 | Gorhan et al. | WO | 9851226 A2 | 11/1998 |
| 2006/0149256 | A1 | 7/2006 | Wagner et al. | WO | WO 99/04718 | 2/1999 |
| 2006/0161157 | A1 | 7/2006 | Mosca et al. | WO | 9921502 A1 | 5/1999 |
| 2006/0200147 | A1 | 9/2006 | Ensign et al. | WO | 9956653 A1 | 11/1999 |
| 2006/0217725 | A1 | 9/2006 | Suh | WO | WO 99/56653 | 11/1999 |
| 2006/0235399 | A1 | 10/2006 | Carls et al. | WO | WO 99/59492 | 11/1999 |
| 2006/0241616 | A1 | 10/2006 | Konieczynski et al. | WO | 0003653 A2 | 1/2000 |
| 2007/0010817 | A1 | 1/2007 | de Connick | WO | WO 00/25689 | 5/2000 |
| 2007/0055251 | A1 | 3/2007 | Huebner et al. | WO | 0066011 | 11/2000 |
| 2007/0123879 | A1 | 5/2007 | Songer et al. | WO | WO 00/78238 | 12/2000 |
| 2007/0162016 | A1* | 7/2007 | Matityahu ............... 606/69 | WO | 0101874 A1 | 1/2001 |
| 2008/0027439 | A1 | 1/2008 | Sasing | WO | 0126566 A1 | 4/2001 |
| 2008/0172094 | A1 | 7/2008 | Mathieu | WO | WO 01/26567 | 4/2001 |
| 2009/0012571 | A1 | 1/2009 | Perrow et al. | WO | 0149191 | 7/2001 |
| 2009/0024170 | A1* | 1/2009 | Kirschman ............... 606/280 | WO | 0164144 A2 | 9/2001 |
| 2011/0112584 | A1 | 5/2011 | Frigg | WO | 0182804 A1 | 11/2001 |
| | | | | WO | 0182805 A1 | 11/2001 |

FOREIGN PATENT DOCUMENTS

| | | |
|---|---|---|
| DE | 2933141 | 4/1980 |
| DE | 4409833 | 10/1995 |
| DE | 19548395 | 9/1997 |
| EP | 0 179695 A1 | 4/1986 |
| EP | 0 201 024 B1 | 11/1986 |
| EP | 0 242 842 B1 | 10/1987 |
| EP | 0 251583 A2 | 1/1988 |
| EP | 251583 A2 | 1/1988 |
| EP | 0 410 309 A1 | 1/1991 |
| EP | 0 455255 A1 | 11/1991 |
| EP | 0 471418 A1 | 2/1992 |
| EP | 471418 A1 | 2/1992 |
| EP | 0502815 | 9/1992 |
| EP | 0 699 057 B1 | 3/1996 |
| EP | 0 809 972 A3 | 12/1997 |
| EP | 0 897 697 A1 | 2/1999 |
| EP | 0897697 | 2/1999 |
| EP | 0 903 113 A2 | 3/1999 |
| EP | 988833 A2 | 3/2000 |
| EP | 995404 A1 | 4/2000 |
| WO | WO 01/82804 | 11/2001 |
| WO | WO 01/82805 | 11/2001 |
| WO | WO 01/89400 | 11/2001 |
| WO | WO 01/89428 | 11/2001 |
| WO | 02076317 A1 | 10/2002 |
| WO | WO 02/080789 | 10/2002 |
| WO | 02098276 A2 | 12/2002 |
| WO | 02098277 A2 | 12/2002 |
| WO | WO 02/098277 | 12/2002 |
| WO | 03007826 A1 | 1/2003 |
| WO | 03017856 A1 | 3/2003 |
| WO | 03053262 A1 | 7/2003 |
| WO | 03063714 | 8/2003 |
| WO | WO 03/071966 | 9/2003 |

OTHER PUBLICATIONS

Omeis et al., "History of Instrumentation for Stabilization of the Subaxial Cervical Spine," Neurosurg Focus 16 (1): Article 10, 2004.

Chang, J.H.; Chang, G.L.; Hsu, A.T.. Kinematic Study of Cervical Vertebrae Adjacent to Fixation Procedures. 1999 Bioengineering Conference, Big Sky, Montana, USA. Jun. 1999. 2 pages.

Tippets, Richard H., MD; Apfelbaum, Ronald I., MD. Anterior Cervical Fusion with the Caspar Instrumentation System. *Neurosurgery*, vol. 22, No. 6, Part 1. Jun. 1998. 6 pages. Lippincott Williams & Wilkins; Hagerstown, MD, USA.

Benzel, Edward, MD; Leon, Steven, MD. Enhancing Cervical Spine Fusion, www.medscape.com. Mar. 2001. 31 pages.

Paramour, Christoper, MD; Dickman, Curtis, MD; Sonntag, Volker, MD. Radiographic and Clinical Follow-Up Review of Caspar Plates in 49 Patents. *Journal of Neurosurgery*, vol. 84, No. 6. Jun. 1996. 5 pages. American Association of Neurological Surgeons; Rolling Meadows, IL, USA.

Clausen, John; Tyken, Timothy, MD; Traynelis, Vincent, MD; Sawin, Paul, MD; Dexter, Franklin, MD; Goel, Vijay. Biomechanical Evaluation of Caspar and Cervical Spine Locking Plate Systems in a Cadaveric Model. *Journal of Neurosurgery*, vol. 84, No. 6. Jun. 1996. 9 pages. American Association of Neurological Surgeons; Rolling Meadows, IL, USA.

Bose, Bikash, MD. Anterior Cervical Fusion Using Caspar Plating: Analysis of Results and Review of the Literature. *Surgical Neurology*, vol. 29, No. 1. Jan. 1998. 8 pages. Elsevier Biomedical; New York, NY, USA.

Pitzen, T.; Steudel, W.; Oxland, T. The Effect of Posterior Element Injury on Cervical Spine Flexibility While Using Anterior Plates With and Without Posterior Fixation. An In Vitro Trauma Model. $52^{nd}$ Annual Meeting of the German Society of Neurosurgery, Bielefeld, Germany. May 2001. 1 page.

Caspar, W; Barbier, DD; Klara, PM. Anterior Cervical Fusion and Caspar Plate Stabilization for Cervical Trauma. *Neurosurgery*, vol. 25, No. 4. Oct. 1989. Lippincott Williams & Wilkins; Hagerstown, MD, USA. 1 page.

Armstrong, Gordon; Chow, Donald. The Contoured Anterior Spinal Plate. *Spinal Instrumentation*. 1992. Williams & Wilkins; Baltimore, MD, USA.

Zdeblick, Thomas, MD; Ghanayem, Alexander, MD; Rapoff, Andrew, MS; Swain, Carol, MS; Bassett, Tim, MD; Cooke, Mary, MS; Markel, Mark, DVM. Cervical Interbody Fusion Cages: An Animal Model With and Without Bone Morphogenetic Protein. *Spine*, vol. 23, No. 7. Apr. 1998. Lippincott Williams & Wilkins; Hagerstown, MD, USA. 8 pages.

Takahashi, Toshiyuki; Tominaga, Teiji; Yoshimoto, Takashi; Koshu, Keiji; Tokobori, A. Toshimitsu; Aizawa, Yoichi. Biomechanical Evaluation of Hydroxyapatite Intervertebral Graft and Anterior Cervical Plating in a Porcine Cadaveric Model. *Bio-medical Materials and Engineering*, vol. 7, No. 2. 1997. IOS Press; Amsterdam, Netherlands. 7 pages.

Chen, Ing-Ho; Yang, Rong-Sen; Chen, Po-Quang. Plate Fixation for Anterior Cervical Interbody Fusion. *Journal of the Formosan Medical Association*, vol. 90, No. 2. Feb. 1991. Scientific Communications International; Hong Kong, China. 4 pages.

Office Action dated Jul. 21, 2011 in related U.S. Appl. No. 12/167,666, 19 pages.

Amendment dated Nov. 21, 2011 filed in related U.S. Appl. No. 12/167,666, 15 pages.

* cited by examiner

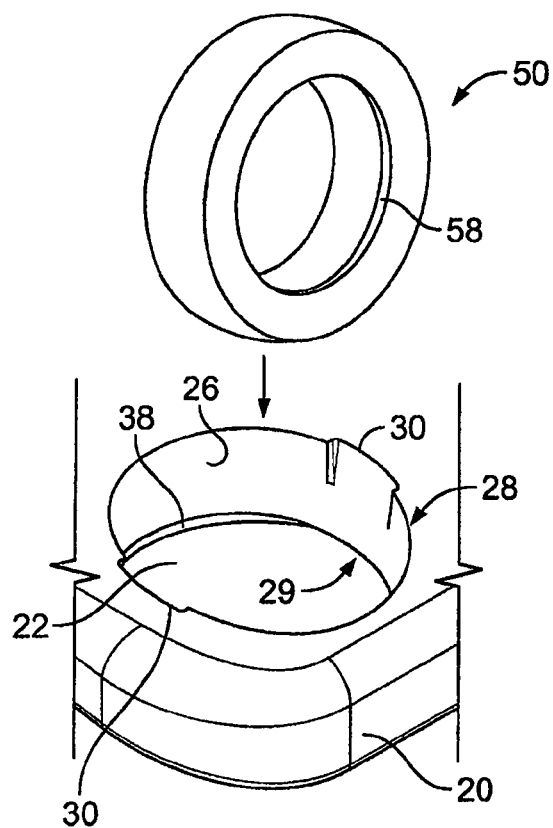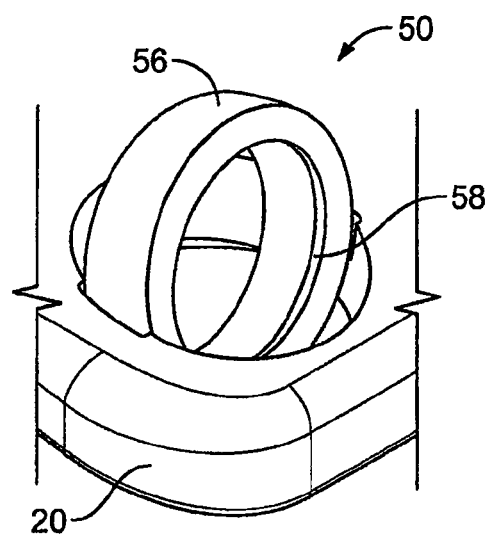
FIG. 7A          FIG. 7B
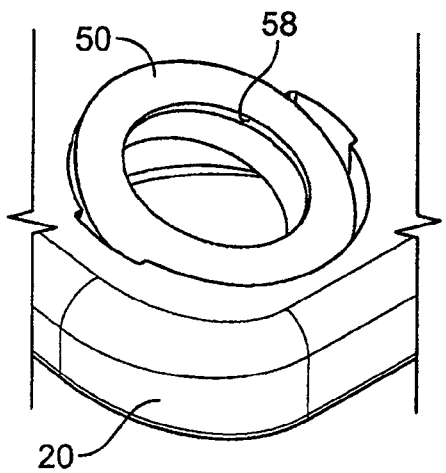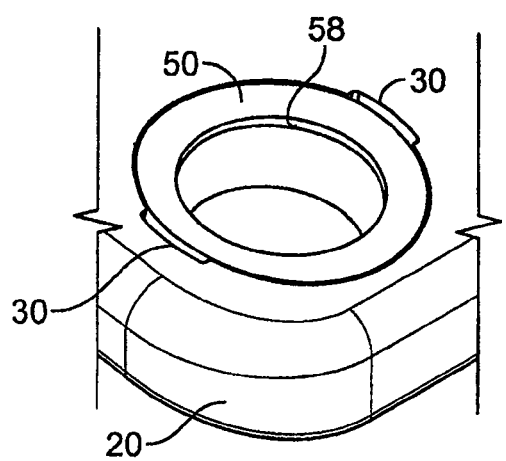
FIG. 7C          FIG. 7D

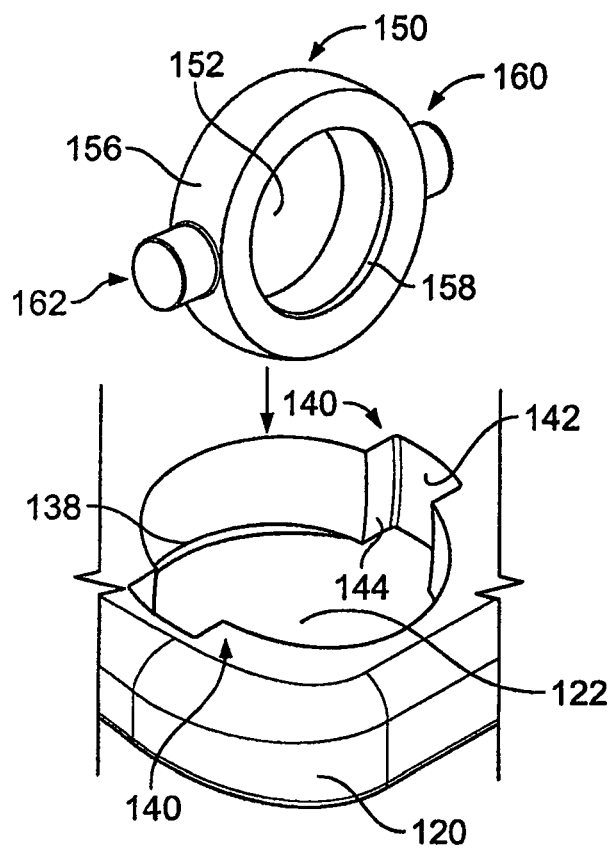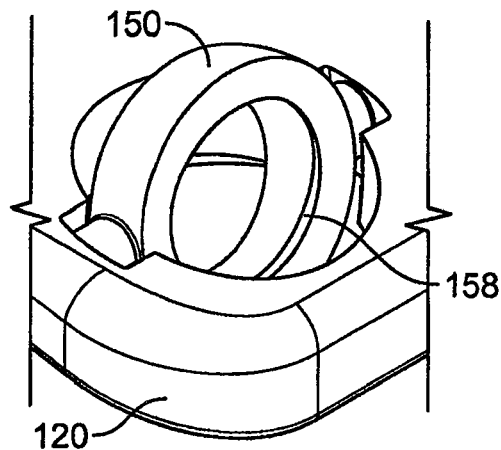
FIG. 18A
FIG. 18B
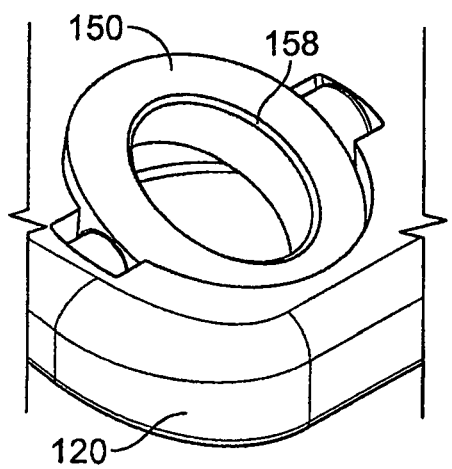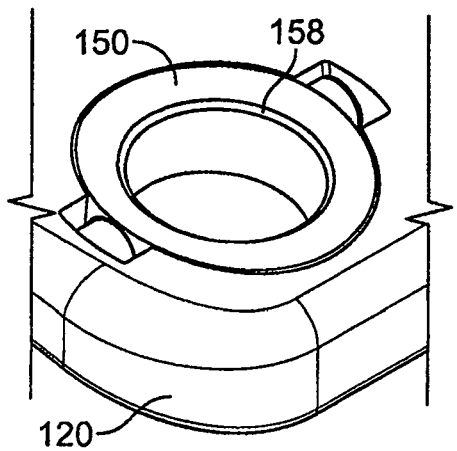
FIG. 18C
FIG. 18D

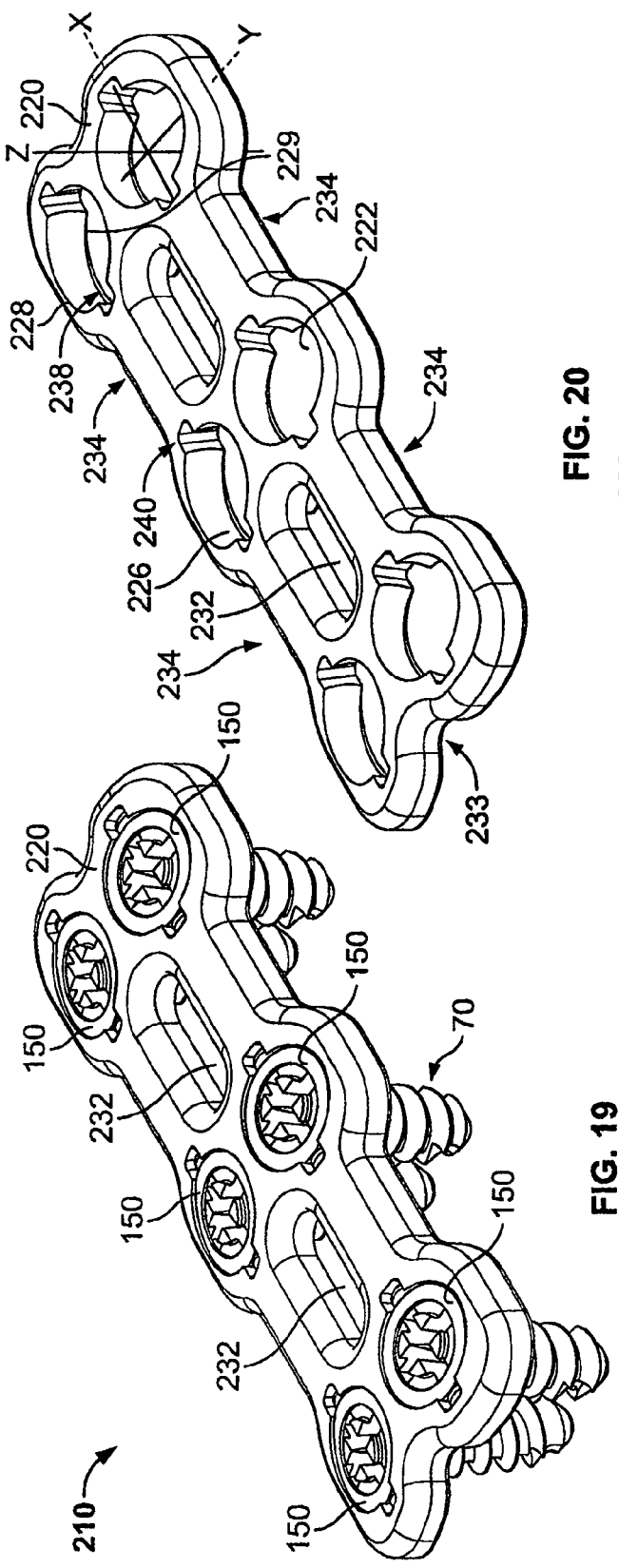
FIG. 19
FIG. 21
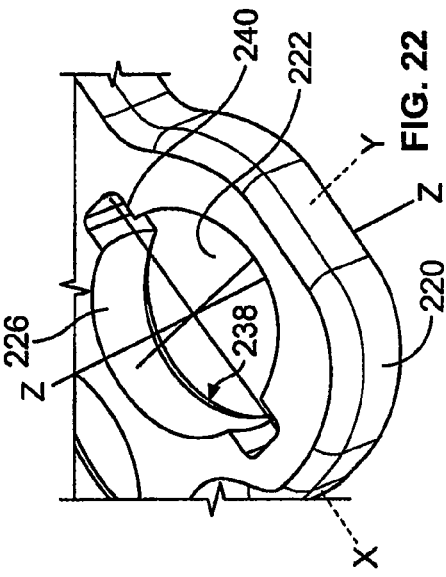
FIG. 20
FIG. 22

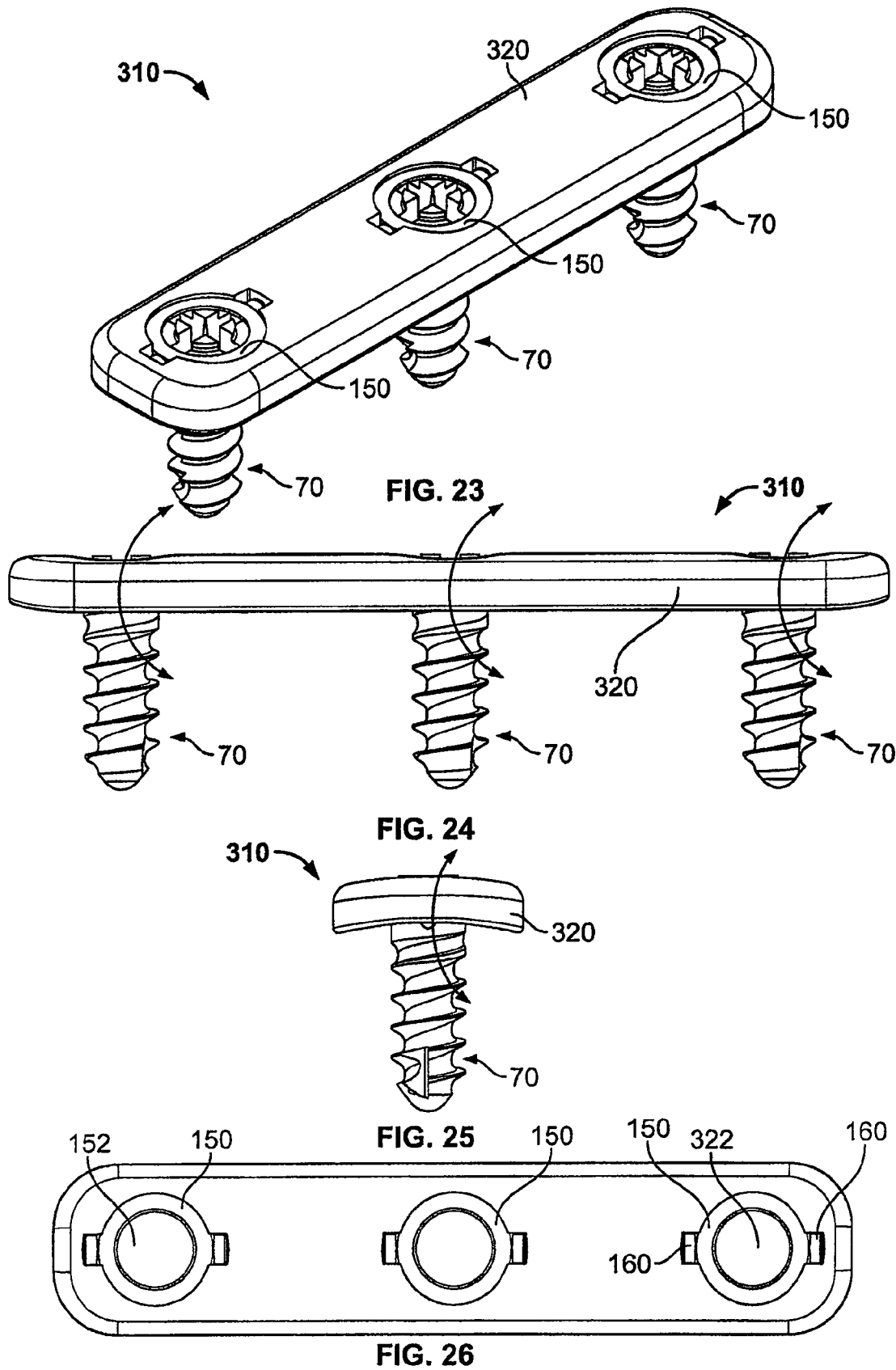

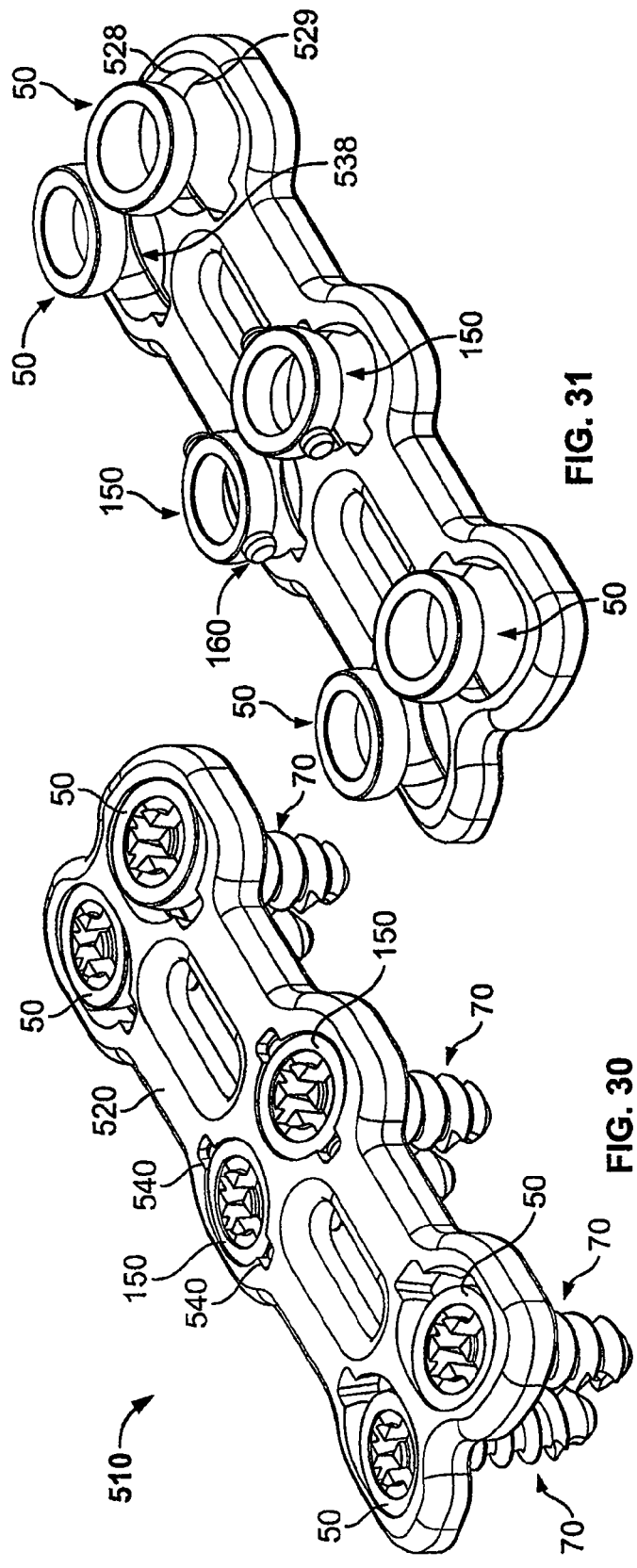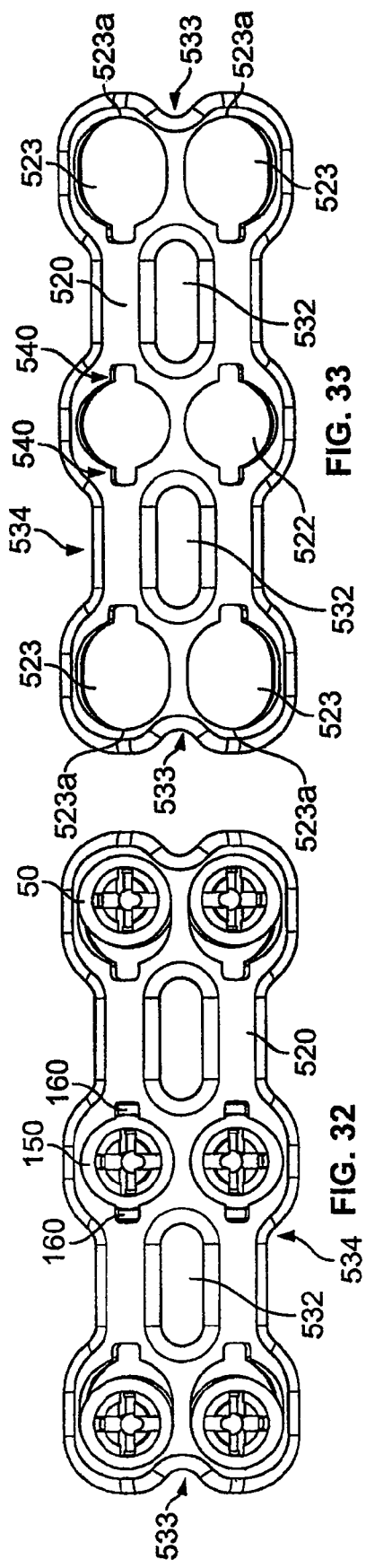

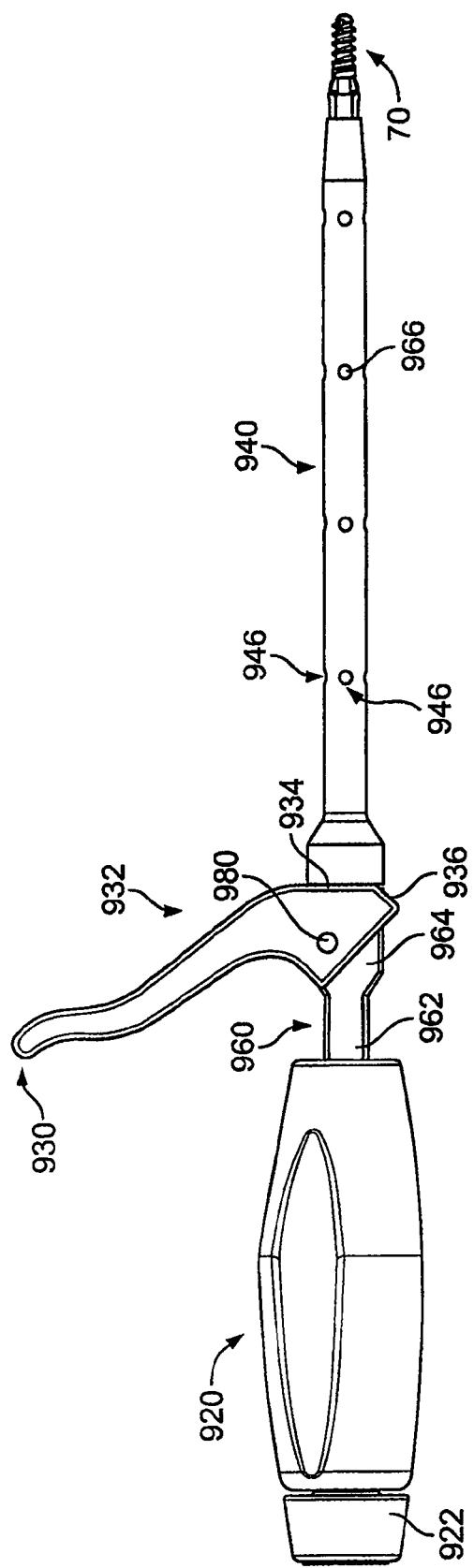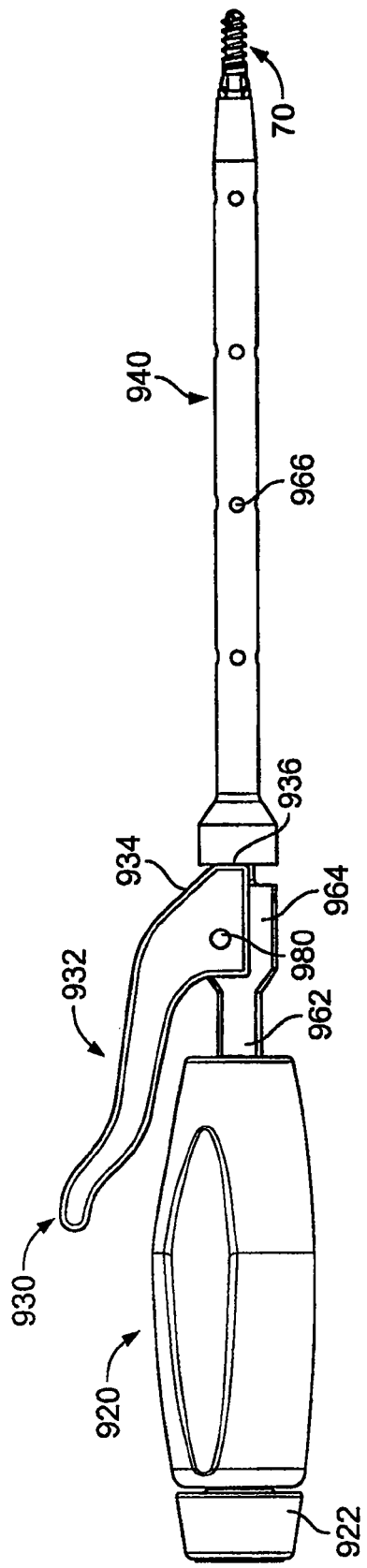

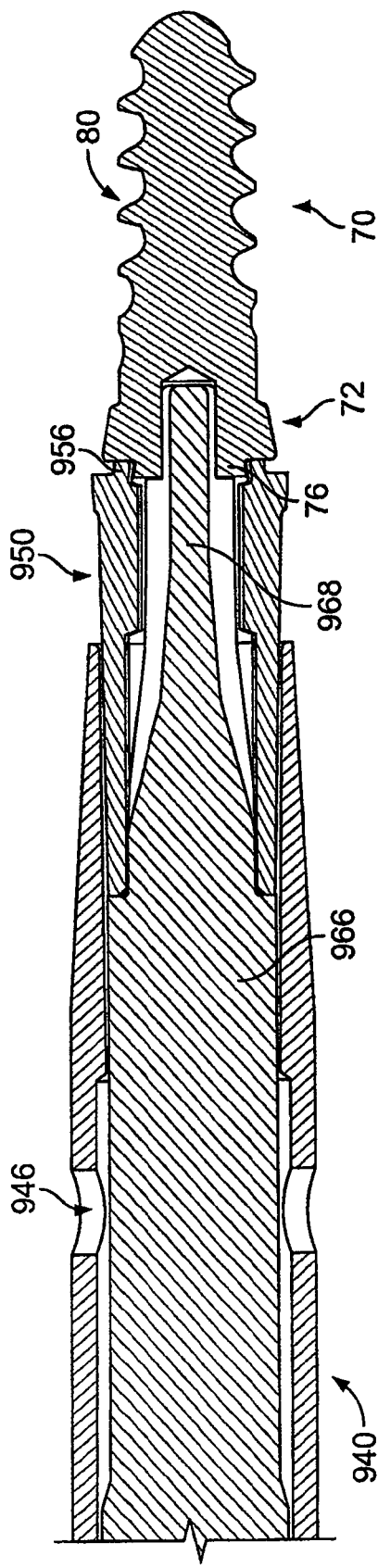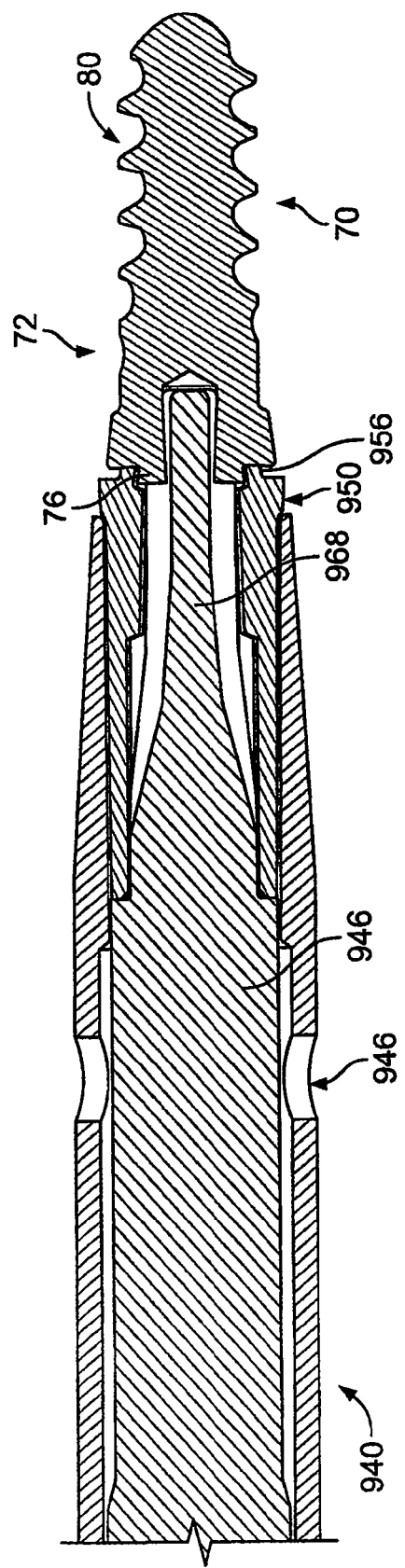

BONE PLATE SYSTEM

CROSS-REFERENCE TO RELATED APPLICATIONS

This application claims priority to U.S. Provisional Application Ser. No. 60/968,233, filed Aug. 27, 2007, and entitled "Bone Plate Systems," which is hereby fully incorporated by reference as if set forth herein. U.S. Provisional Application Ser. No. 60/947,873, filed Jul. 3, 2007, and entitled "Bone Plate System" is also fully incorporated by reference as if set forth herein.

FIELD OF THE INVENTION

The invention relates to bone plate systems and, more particularly, to a bone plate system that allows for motion of the bone anchors relative to the bone plate member.

BACKGROUND OF THE INVENTION

There are presently many different types of plate and fixture systems for securing two or more bones or bone fragments in relative position so that the bones may fuse or heal, or so that tissue adjacent the bones may heal without disruption from the movement of the secured bones. As used herein, the term bone may refer to a bone, or a bone fragment or portion, and the term may refer to a portion of a bone that is covered with another material, such as the endplates covering the top and bottom surface of a vertebra. Also as used herein, the term fusion refers to the joining of materials, such as bone or graft material, and the fusion site is the entire region in which fusion may be desired. These systems have been used to secure spinal vertebrae such as cervical vertebrae.

Bone plate systems are typically used to assist or direct spinal fusion or vertebral healing procedures. These procedures promote earlier post-operative patient mobility and improve success in correcting spinal deformities while decreasing the need for post-operative collars and the incidence of graft dislodgement if a graft is used.

Furthermore, these systems have been found to assist in controlling and/or exerting a compressive loading force applied to the surgical site. By applying a compressive load, it has been found that bone heals more optimally and with greater integrity, a principle known as Wolff's Law.

Some prior bone plate systems seek to provide a compressive force while allowing the vertebrae to settle naturally under the force of gravity by offering bone anchors such as screws or alternatively coupling members that couple the screw heads to the bone plates that can pivot with respect to the plate as the vertebrae shift, settle, and/or curvature of the spine is altered. Many previous bone plate systems do not even allow such motion, and many that do provide inadequate control over the manner in which the vertebrae settle under compression. Additionally, if this shifting or settling of vertebrae is improperly or inadequately accounted for, additional stress may be added to the vertebrae and an undesirable load path through the spine may be created, hindering the recovery, grafting, and/or fusion process.

Another manner for permitting compressive loads between joined bones is to utilize a dynamic plate having at least one elongated screw aperture that allows settling of the vertebrae by gravity by allowing at least one secured bone and its associated bone anchor to move relative to the plate. However, heretofore known arrangements of standard and dynamized apertures in such plates provide less than optimal capacity for controlling the movement and/or compression between more than two tiers of secured vertebrae and/or many previously known bone plates did not provide sufficient movement to allow the spine to settle naturally as a portion of the spine is compressed during the recovery period. Inasmuch as these prior bone plate systems allowed for some settling of the spine, this settling would cause the spine to be inclined to exhibit an altered degree of curvature, which prior dynamic bone plate systems failed to accommodate. If the spine is not allowed to adapt to this different degree of curvature and thus reach a more stable configuration, an undesirable or improper load path through the spine may be created, hindering the recovery, grafting, and/or fusion process.

Another shortcoming of many bone plate systems is the backing out or loosening of the bone anchors, which are often bone screws. If the bone anchors loosen and/or back out, the bones are not properly secured and may be allowed to move relative to one another in an uncontrolled manner. This may compromise the ability to achieve optimal bone fusion and bone alignment, and it may lead to loss of graft material and damage or loss of bone. Furthermore, when the plate is a dynamic or dynamized plate, such that at least some bone anchors may be permitted to move relative to the plate, these issues may be further compounded or exacerbated by a bone anchor backing out. Additionally, in the case of anterior cervical plates, a bone anchor backing out could hinder swallowing and cause irritation or even a puncture wound to the esophagus, which may lead to infection or even death.

Some known bone plate systems offer resilient base members such as c-clips which house at least a portion of the head of the bone anchor. Often, the base member will be compressed upon entering a throughbore and allowed to expand at least partially to its original shape. These resilient base members, however, have clear drawbacks. First, under certain conditions, many resilient base members may be recompressed and pushed out of the throughbore, which may allow the base member and/or bone anchor to loosen and back out of the bone plate. Furthermore, resilient base members often expand only partially to their original configuration, thus imposing stress to the inner walls of the throughbore, causing increased friction and thus hindering the bone anchor from accommodating spinal shifts, compression, and/or changes in curvature.

Accordingly, there is a need for improved bone plates, bone plate systems, mechanisms to inhibit bone anchor back-out, and improved tools and methods for utilizing bone plate systems.

SUMMARY OF THE INVENTION

In accordance with the present invention, several embodiments of bone plate systems as well as tools and methods for installing the same are provided. The present bone plate systems overcome shortcomings of prior bone plate systems and generally allow motion for the bone anchors such that they may move relative to the bone plates to accommodate shifting or settling of secured vertebrae while offering desirable levels of control and predictability of this motion. Furthermore, one exemplary embodiment featuring aspects according to the present invention represents a new and novel approach to combining a narrow bone plate profile with enhanced torsional stability.

In one form of the present invention, a bone plate system is provided having an elongate plate member and a plurality of throughbores of the plate member. A pivot base is received in one of the throughbores with the pivot base having an opening configured to seat the head end of a bone anchor that may be driven into spinal bone. The base member and throughbores have cooperating surfaces allowing the pivot base and corresponding bone anchor member to freely shift or pivot within the throughbore relative to the plate member. In this way, the pivot base can exhibit well-controlled pivoting motion relative to the plate to allow the spine to settle to a desirable configuration and accommodate shifts in spinal curvature as well as form a stable and favorable load path through the spine.

In another form of the present invention, a bone plate system is provided having an elongate plate member extending along an axis thereof and a plurality of throughbores of the plate member. The throughbores are configured to receive a base member which has a bone anchor member driven therethrough, the head end of the bone anchor member able to be seated within an opening in the base member. The base member has a substantially rigid body, and seating the head end of the bone anchor therein does not deform the body of the base member. The rigid base portion and the throughbore of the bone plate member are configured to allow controlled motion of the base member and associated bone anchor member relative to the plate member even after the bone anchor member has been driven into bone and the head end of the bone anchor member has been seated within the opening of the base member. In this way, rigid base members are provided that exhibit controlled motion relative to the plate to accommodate spinal shifting and/or changes in spinal curvature.

In one form of the present invention, a bone plate system is provided having an elongate plate member with a plurality of throughbores extending therethrough. Each throughbore is configured to receive a retainer base member, each retainer base member having an opening to receive a bone anchor member having a head end which is seated within the opening of the base member. The base member opening has a retention portion sized to keep the one bone anchor member head end seated within the opening and keep the bone anchor member from backing out therefrom. Additionally, the base member opening has cooperating surfaces of the base member and the throughbore of the plate member allow for pivoting and, optionally, translation of the base member and bone anchor member relative to the plate member even with the bone anchor member driven into bone and the head end of the bone anchor member seated in the opening of the retainer base member. Thus, settling of the vertebrae and changes in spinal curvature may be accounted for, which is desirable because if pivoting alone may not account for the expected settling of a patient's vertebrae, a harmful load path may be created through the spine, hindering the recovery, grafting, and/or fusion process.

In another form of the present invention, a bone plate system is provided having an elongate bone plate member with a plurality of throughbores of the plate member. At least one of the throughbores has at least one access slot in communication therewith whereby a base member may be inserted into the throughbore. The base member is inserted into the throughbore through the access slots in an insertion orientation and is then shifted to a seated orientation within the one throughbore.

In one form, the base member has at least one pivot or projecting member extending from the base member into access cavities defining confronting extending surfaces that extend from the main throughbore portion to keep the base member and corresponding bone anchor member from turning in the throughbore due to torque applied to the base member via the seated head of the bone anchor member. In this way, the opposing walls of the confronting surfaces of the access slot or cavity may contact the extended portions of the base member and guide pivotal motion thereof while enhancing the overall torsional stability of the bone plate system, allowing the plate member to have a narrow or monoplate configuration in some embodiments of the present invention while maintaining desirable mechanical properties. Bone plate systems with more narrow profiles tend to cause less irritation or harm to the surrounding soft tissues, and, in the case of anterior cervical plates for example, a narrow plate member profile may result in less encroachment and/or irritation to the esophagus.

In one form of the present invention, bone plate systems are provided, the systems having a bone plate with at least one throughbore therein. In a preferred form, the plate features one throughbore per level or tier, each throughbore being configured to receive a pivot base therein. Cavities or grooves extending from the main throughbore portions and extended members of the pivot bases feature opposing sides and as a result the throughbores and pivot bases allow pivoting of the pivot bases while providing enhanced torsional stability to the bone plate systems and inhibiting rotation with respect to only one primary axis while allowing rotation with respect to the other two primary axes.

In another form, a method is provided whereby a base member is seated within a bone plate, the base member being aligned with access slots of a throughbore, inserted into the access slots in an insertion orientation, and then rotated into a seated orientation within the throughbore.

In one form, a method is provided whereby a bone plate is secured to bone, the method comprising compressing a resilient head portion of a bone anchor member with an insertion tool engaged therewith, driving the bone anchor member into bone, seated the compressed head portion within a base member opening, and releasing the insertion tool from the resilient head portion of the bone anchor member so that the bone anchor member is retained within the opening and kept from backing out of the base member.

In some forms, the bone plate is an anterior cervical plate, and during installation of the bone plate system, the plate is placed over a plurality of cervical vertebrae with each tier and corresponding throughbores in the bone plate aligned to a corresponding individual vertebra, forming two rows of throughbores. Two bone anchors per tier are driven into a corresponding vertebra, with the head end of each bone anchor being seated in the opening defined by each pivot base such that the bone anchor and pivot base pivot and, in the case of a dynamized throughbore, translate as one relative to the plate with the pivot base and bone anchor are fixed relative to one another.

Additionally, in some forms, the bone plate is an anterior cervical plate, and during installation of the bone plate system, the plate is placed over a plurality of cervical vertebrae with each tier and corresponding throughbore in the bone plate aligned to a corresponding individual vertebra, forming a single row of throughbores. One bone anchor per tier is driven into a corresponding vertebra, with the head end of each bone anchor being seated in the opening defined by each pivot base such that the bone anchor and pivot base pivot as one relative to the plate with the pivot base and bone anchor fixed relative to one another.

In one form, the extended members from pivot bases offer the bone plate system enhanced torsional and rotational stability, meaning that the pivot base and adjoined extended members add to the overall torsional resistance of the bone plate system and aid in rotating or twisting of the coupled vertebrae relative to one another in a manner that may hinder the recovery process by, for example, damaging a graft site or weakened vertebra. In addition, the monoplate or narrow-profile embodiments of the bone plate may cause less irritation to the esophagus and other soft tissues while allowing the bone plate system to be installed with a smaller incision than is necessary for bone plates with wider profiles. Furthermore, using only one bone anchor per tier may allow a shortened installation time, a bone plate system that is easier and less costly to manufacture, and cause less degradation to the structural integrity of the vertebrae.

In another form, the geometric configuration between the bone plate and the pivot bases provides clearances that accommodate the pivoting motion of the pivot bases relative to the plate. In a preferred form, this pivoting motion has a predetermined defined range. Due to the clearances, the geometric configurations, and the generally spherical profiles of the pivot bases and the internal surfaces of the throughbores in the bone plate, the pivot bases without extended member are generally free to pivot and/or rotate about any axis and the pivot bases with extended members are generally free to pivot fore and aft and side to side relative to the longitudinal axis of the plate while being inhibited from rotating with respect to the central axis of the throughbore of the plate member. The freedom to pivot allows the bone plate system to accommodate at least a portion of the settling of the coupled vertebrae during the recovery period, as well as adapt to changes in spinal curvature. Generally, in the case of a three-tiered bone plate, the uppermost and lowermost bone screws will be installed at diverging angles with respect to one another, and as the vertebrae settle, these angles tend to relax.

In one form, the geometric configuration between the bone plate and the pivot bases features elongated or dynamized throughbores wherein the pivoting relationship is the same as described above, but the elongation of at least one throughbore provides the pivot base received therein with the ability to translate as well as pivot relative to the bone plate. Generally, at least one throughbore is a standard or non-dynamized throughbore, and the pivot bases disposed within dynamized or elongated throughbores are generally moved as far away from the standard throughbore as possible before the bone anchors are inserted. A dynamic bone plate may be used when a surgeon or specialist believes that the vertebrae to be secured to the plate member may experience more settling or shifting than pivoting alone could account for. In this case, the compressive forces and shifting of the vertebrae cause the dynamized throughbores to allow the pivot bases disposed therein to demonstrate controlled translational motion toward the standard throughbore as well as a predetermined range of angular motion, both working to accommodate settling of the vertebrae and possible changes in curvature. This combination may allow the spine more freedom to settle to a more stable configuration, which may lead to a more desirable load path through the spine and better promote the recovery, grafting, and or/fusion process.

In another form according to other aspects of the present invention, a surgical instrument for driving a bone anchor is provided. The surgical instrument comprises a bone anchor engagement portion, a compression shaft, and a lever for actuating the compression shaft. Actuation of the compression shaft can move the compression shaft relative to an engaged bone anchor member, effecting compression and uncompression of a resilient head portion of the bone anchor member.

BRIEF DESCRIPTION OF THE DRAWINGS

FIG. 7A is a step from the procedure of FIG. 7;

FIG. 7B is a step from the procedure of FIG. 7;

FIG. 7C is a step from the procedure of FIG. 7;

FIG. 7D is the end of the procedure of FIG. 7 with the pivot base seated within the throughbore of the plate;

FIG. 18A is a perspective view of a portion of the bone plate system of FIG. 14 showing a step of a procedure whereby a pivot base may be seated within a throughbore of the plate;

FIG. 18B is a step of the procedure of FIG. 18A;

FIG. 18C is a step of the procedure of FIG. 18A;

FIG. 18D is the end of the procedure of FIG. 18A with the pivot base seated within the throughbore of the plate;

FIG. 19 is a perspective view a bone plate system embodying features in accordance with the present invention;

FIG. 20 is a perspective view of the plate of the bone plate system of FIG. 19;

FIG. 21 is a top view of the bone plate system of FIG. 19 with the bone anchors removed;

FIG. 22 is a perspective view of a portion of the plate of FIG. 20;

FIG. 23 is a perspective view of a bone plate system embodying features in accordance with the present invention;

FIG. 24 is a side view of the bone plate system of FIG. 23;

FIG. 25 is an end view of the bone plate system of FIG. 23;

FIG. 26 is a top view of the bone plate system of FIG. 23 with the bone anchors removed;

FIG. 30 is a perspective view of a bone plate system having features in accordance with the present invention;

FIG. 31 is a perspective view of the bone plate system of FIG. 30 with the bone anchors removed and the pivot bases exploded;

FIG. 32 is a top view of the bone plate system of FIG. 30;

FIG. 33 is a top view of the plate of the bone plate system of FIG. 30;

FIG. 36 is a side view of the driver and the bone anchor of FIG. 34;

FIG. 37 is a side view of the driver and the bone anchor of FIG. 35;

FIG. 41 is a cross-sectional side view of a portion of the driver and the bone anchor of FIG. 34;

FIG. 42 is a cross-sectional side view of a portion of the driver and the bone anchor of FIG. 35;

DETAILED DESCRIPTION OF THE PREFERRED EMBODIMENTS

Figure 2:
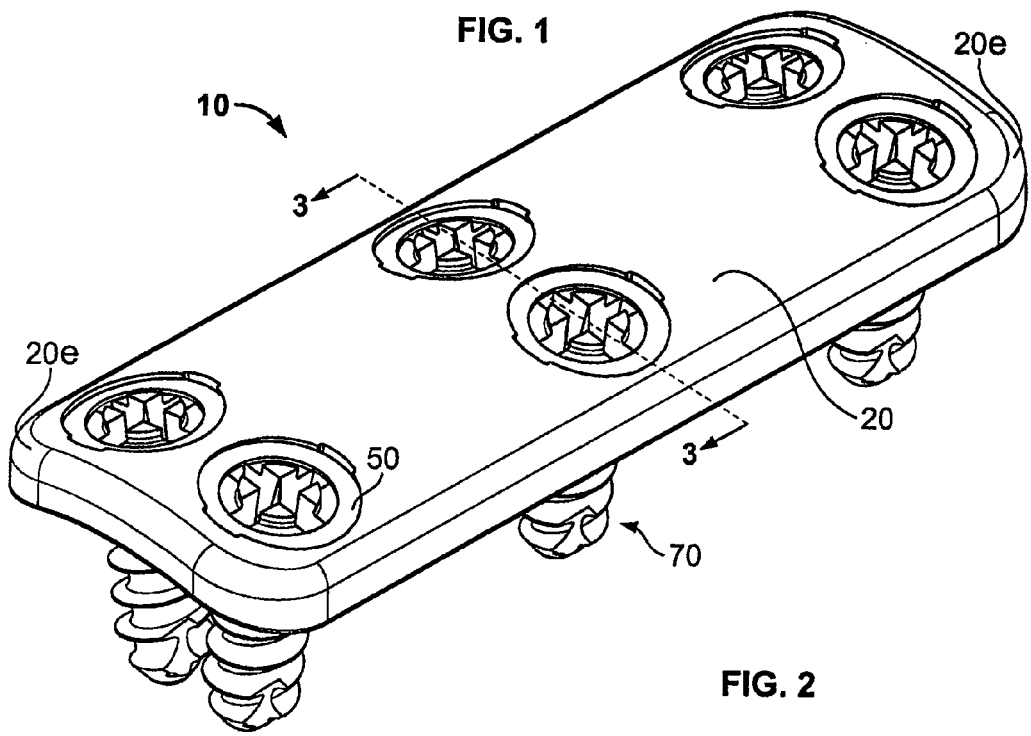
FIG. 2 is a perspective view of the bone plate system of FIG. 1.

Generally speaking, pursuant to these various embodiments, bone plate systems are disclosed herein for securing a plurality of bones 7 in a desired orientation and arrangement. In some forms, the bone plate system utilizes a dynamized plate with dynamic throughbores so that bones 7 may compress and shift toward each other, such as with dynamic or dynamized bone plate systems 410, 510 shown in FIGS. 27 and 30, respectively. In other forms, bone plate systems utilize standard plate members with throughbores of the same size, such as with standard or non-dynamized bone plate systems 10, 110, 210 shown in FIGS. 2, 14, and 19, respectively. In other forms, the bone plate systems utilize monoplate or single-row or single screw per vertebral level embodiments, such as with the monoplate bone plate system 310 shown in FIG. 23.

Figure 1:
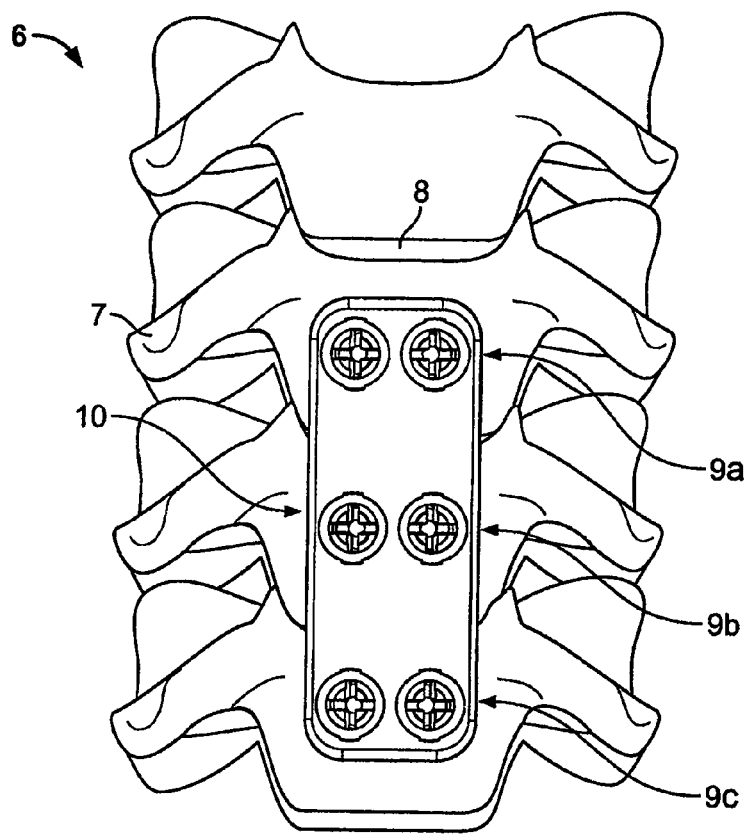
FIG. 1 is a top plan view of a bone plate system embodying features in accordance with the present invention, the bone plate system installed in the anterior cervical region of a spinal column.

Referring to FIGS. 1-13, a standard bone plate system 10 is shown which may assist in the healing and repair of damaged, fractured, or broken bones. In the exemplary illustration of FIG. 1, bones 7 are adjacently located vertebrae of a spine 6 spaced from one another by a spinal disc 8. The bone plate system 10 may also be used to assist in the healing necessary after trauma has been experienced by the spinal disc 8 and/or a disc 8 has been removed from an intervertebral space. For example, the bone plate system 10 may be utilized for stabilization and securement when adjacent vertebrae 7 are fused, with or without the assistance of a bone graft between the vertebrae 7. Furthermore, the bone plate system 10 may be used to correct and/or relieve symptoms of a variety of spinal disorders, which may include but are not limited to degenerative disorders, disorders induced by trauma, and pinched nerves.

In each of these examples, the bone plate system 10 is used to secure the bones 7 (and any prosthetic or graft) in a desired spatial relationship. Typically, the desired spatial relationship between the bones 7 (vertebrae) is generally vertical, such as the vertebrae 7 would be in a normal, healthy spine when the person is standing. As discussed above with respect to Wolff's Law, compression or loading of bones promotes healing of the bones or bone fragments and improves the integrity of the fusion therebetween. Particular to some bones in the human anatomy, such as a femur, the weight of the person, due to gravity, compresses those bones. For spines, the fusion of adjacent vertebrae can similarly benefit from using gravity to compress the adjacent vertebrae 7.

Accordingly, though the bones 7 are secured in a desired spatial relationship, the present bone plate system 10 preferably allows the bones 7 to undergo a certain degree of shifting relative to each other. In other words, to capitalize on the compression imparted to the adjacent vertebrae 7 by gravity, the bone plate system 10 is configured to allow the bones 7 to compress in a manner dictated by the bone plate system 10. In the present system 10, this shifting is preferably accommodated by pivotal motion of pivot members such as pivot bases 50.

The bone plate system 10 generally includes a bone plate member 20 secured to the bones 7 with bone anchors that are, in a preferred form, bone screws 70. The plate member 20 includes throughbores 22 formed therein with a generally spherical pivot base 50 secured within each throughbore 22. The bone screws 70 have a head portion 72 that may be secured within an opening 52 of the pivot base 50 by an retention mechanism that is inherent to the bone plate system 10 based on the configuration of the head portion 72 and the pivot base 50.

The bone plate 20 may be provided with curvature in the longitudinal direction that contours the plate member 20 to the average natural curvature of the spine 6, as well as to reduce interference with surrounding tissues. The plate 20 may be pre-bent to have a curvature in a longitudinal direction, preferably with a radius of curvature of approximately 200 millimeters, and in a lateral direction, preferably with a radius of curvature of approximately 20 millimeters. It is often desirable to alter the standard shape of the plate 20 to fit an individual patient's unique anatomy. This should be done in a manner so as not to scratch or mar the surfaces of the bone plate 20, which otherwise may negatively affect the long-term fatigue performance of the plate member 20. For this purpose, a plate bending instrument may be used for altering the curvature of the plate 20 when necessary due to a unique anatomy. The plate bender is operated to either increase or decrease the radius of the lordotic curvature of the bone plate 20.

The particular embodiment of the present invention shown in FIGS. 1-13 is a standard or non-dynamized bone plate system 10 which may be installed within the anterior cervical region of a spinal column 6. As shown in FIG. 5, the bone plate 20 preferably has a curved profile that contours to the vertebral bones 7 for a complimentary fit. As shown in FIG. 5, the bone plate 20 may extend generally straight relative to the longitudinal axis of the plate 20, but as mentioned previously, plate member 20 may be bent to accommodate the desired curvature of a particular segment of the spinal column 6. The bone plate 20 features two rows of throughbores 22 forming pairs or sets of throughbores 22. Each pair of throughbores 22 will allow two bone anchors to be driven into each vertebra 7. Each throughbore 22 features a curved inner surface 26 terminating in an upper edge or rim portion 28 and a lower edge or rim portion 29, the lower rim portion 29 preferably having at least one retention lip 38 which may act to limit the range of motion of a pivot base 50 seated within a throughbore 22. The generally rectangular plate member 20 has an upper surface 20a, a lower bone-contacting surface 20b, generally straight side portions 20c, and generally straight end portions 20d. The bone plate 20 preferably features rounded edges 20e to minimize irritation and/or damage to the surrounding tissues.

Figure 7:
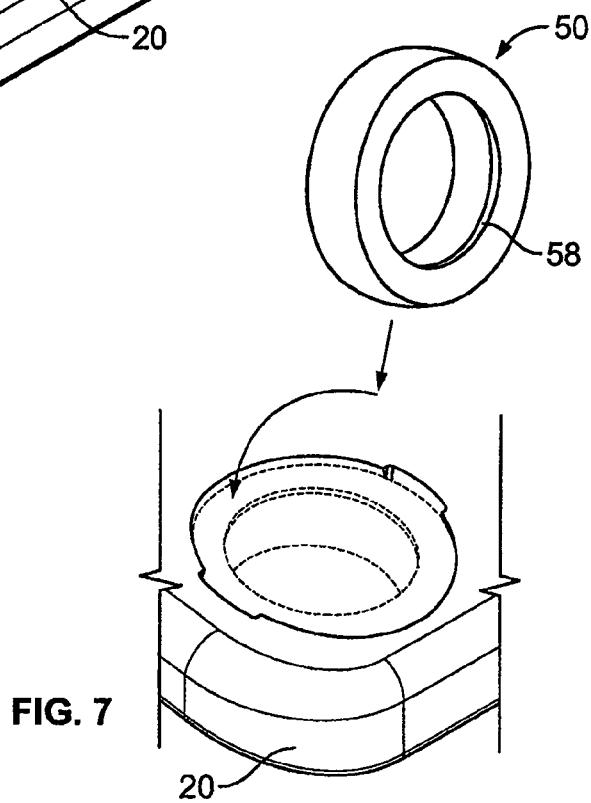
FIG. 7 is a perspective view of a portion of the bone plate system of FIG. 4 demonstrating a procedure whereby a pivot base may be seated within a throughbore of the plate.
Figure 8:
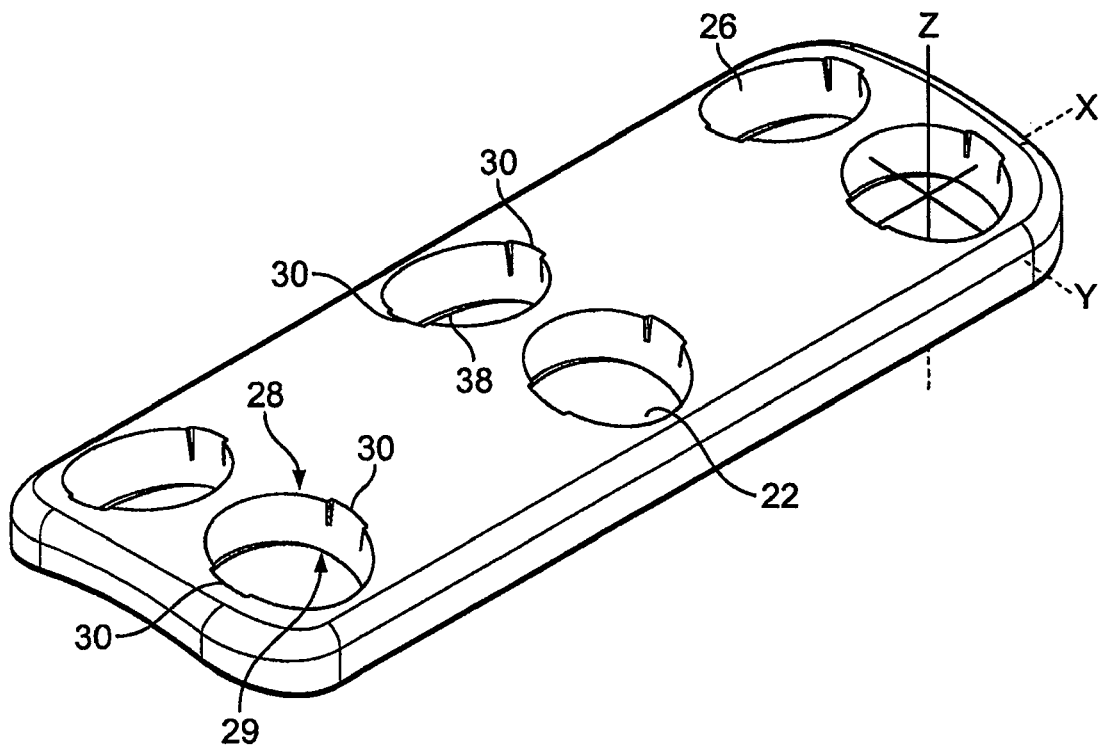
FIG. 8 is a perspective view of the plate of the bone plate system of FIG. 2.
Figure 9:
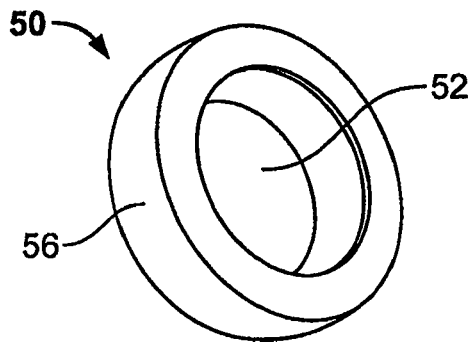
FIG. 9 is a perspective view of a pivot base of the bone plate system of FIG. 2.
Figure 10:
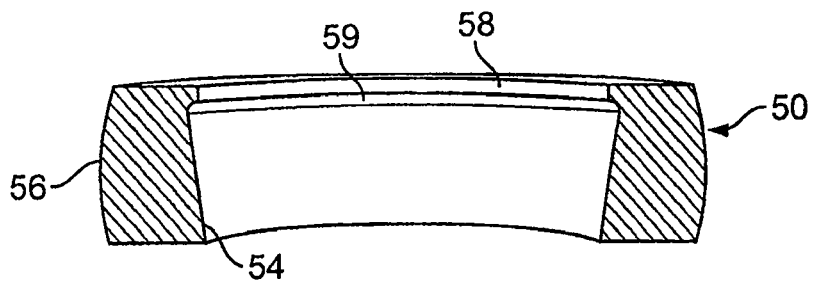
FIG. 10 is a cross-sectional side view of the pivot base of FIG. 9.

A pivot base 50 may be seated within each throughbore 22, and each throughbore 22 preferably features a plurality of access slots 30 to allow the pivot base 50 to enter the throughbore 22. As shown in FIG. 7, the pivot base 50 is inserted in alignment with the insertion notches 30 to allow the pivot base 50 to move past the upper edge or rim portion 28 of the throughbore 22. Preferably, the curved inner surface 26 of the throughbore 22 is complementary to a curved outer profile 56 of the pivot base 50. In this way, as shown in FIGS. 7 and 7A-7D, the pivot base 50 is inserted into the throughbore 22 in alignment with the access notches or insertion grooves 30 and then rotated or rolled into position much like a sphere may be rolled within a spherical pocket. In a preferred form, the throughbores 22 of the plate 20 feature retainment lips 38 that interfere with the pivot base 50 as the pivot base 50 is rolled or rotated into a seated position as shown in FIG. 7D. The substantially rigid pivot base 50 may be forced past the retainment lip 38, preferably causing no permanent or plastic deformation to the lip 38 or the pivot base 50 and allowing the pivot base 50 to roll or rotate past the lip 38 and be seated within the throughbore 22.

In this way, the substantially rigid pivot bases 50 may be seated within the throughbores 22 of the substantially rigid plate member 20 and may not be removed unless the pivot base 50 is returned to alignment with the access grooves 30, which would not be possible if a bone anchor such as a bone screw 70 extended through an opening 52 of a pivot base 50. When seated within the throughbore 22, the concave curvature of the throughbore wall 26 and the convex curvature of the pivot base outer surface 56 results in interfering dimensions, meaning that with the pivot base 50 and the plate member 20 being substantially rigid, the pivot base 50 could not be forced out of the throughbore 22 because the upper and lower rim portions 28, 29 would interfere with the outer surface 56 of the pivot base 50, as an outer diameter $d_3$ of the base member 50 is larger than an upper rim diameter $d_4$. A seated pivot base 50 could only be removed from the throughbore 22 by utilizing the access notches 30.

The pivot base 50 is free to move within the throughbore 22 relative to the plate 20 with the outer surface 56 of the pivot base 50 forming an articulating surface much like a sphere in a spherical pocket along the inner surface 26 of the throughbore 22. Thus, the pivot base 50 remains substantially within the throughbore 22 and is retained therein by the retention lips 38, as may be seen in FIG. 5. The dimension $d_5$ across the throughbore 22 from the edge of one access slot 30 to the edge of the other is preferably just large enough to allow a clearance fit whereby the pivot base 50 may be slidably inserted and then be spherically engaged or made flush with a portion of the curved inner surface 26 of the throughbore 22, as seen in FIG. 7B. The insertion notches 30 preferably extend only approximately halfway down the inner surface 26 of the throughbore 22 so that the generally spherical profile 56 of the pivot base 50 is mated or made flush with the spherical profile 26 of the throughbore 22 and the pivot base 50 is able to be rolled thereon, whereas if the access slots 30 extended through to the bottom surface 20b of the plate member 20, the pivot bases 50 could foreseeably be slidably moved within the access notches through the plate 20 and fall out of the other side thereof.

The pivot base retention lips 38 of the throughbores 22 prevent the pivot bases 50 from rotating or pivoting more than a predetermined amount within the throughbores 22. In this way, a pivot base 50 is free to pivot within the throughbore 22 only until the pivot base 50 contacts the retention lip 38. Once installed or seated within the throughbore 22, the pivot base 50 is inhibited by the retention members 38 from rotating or rolling such that the base member 50 may be realigned with the insertion notches 30 and come out of a seated configuration with the throughbore 22 and possibly be removed from the plate 20 itself. In a preferred form, the minimum load required to overcome the retention lip 38 to seat the pivot base 50 within the throughbore 22 is greater than the maximum load that is anticipated between the pivot base 50 and the retention lip 38 in other situations such as during transporting of the plate system 10 that may occur prior to the plate being implanted. It should be noted that due to the relatively thin profile of the retention lip 38, the remainder of the plate member 20 and the base member 50 are substantially more rigid than the retention lip. In the present embodiment, the access notches 30 are offset from the retention lips 38 so that the outer surface 56 of the base member 50 may be made flush with the inner surface 26 of the throughbore, the generally spherical surfaces 26, 56 facilitating rotational motion therebetween.

Figure 3:
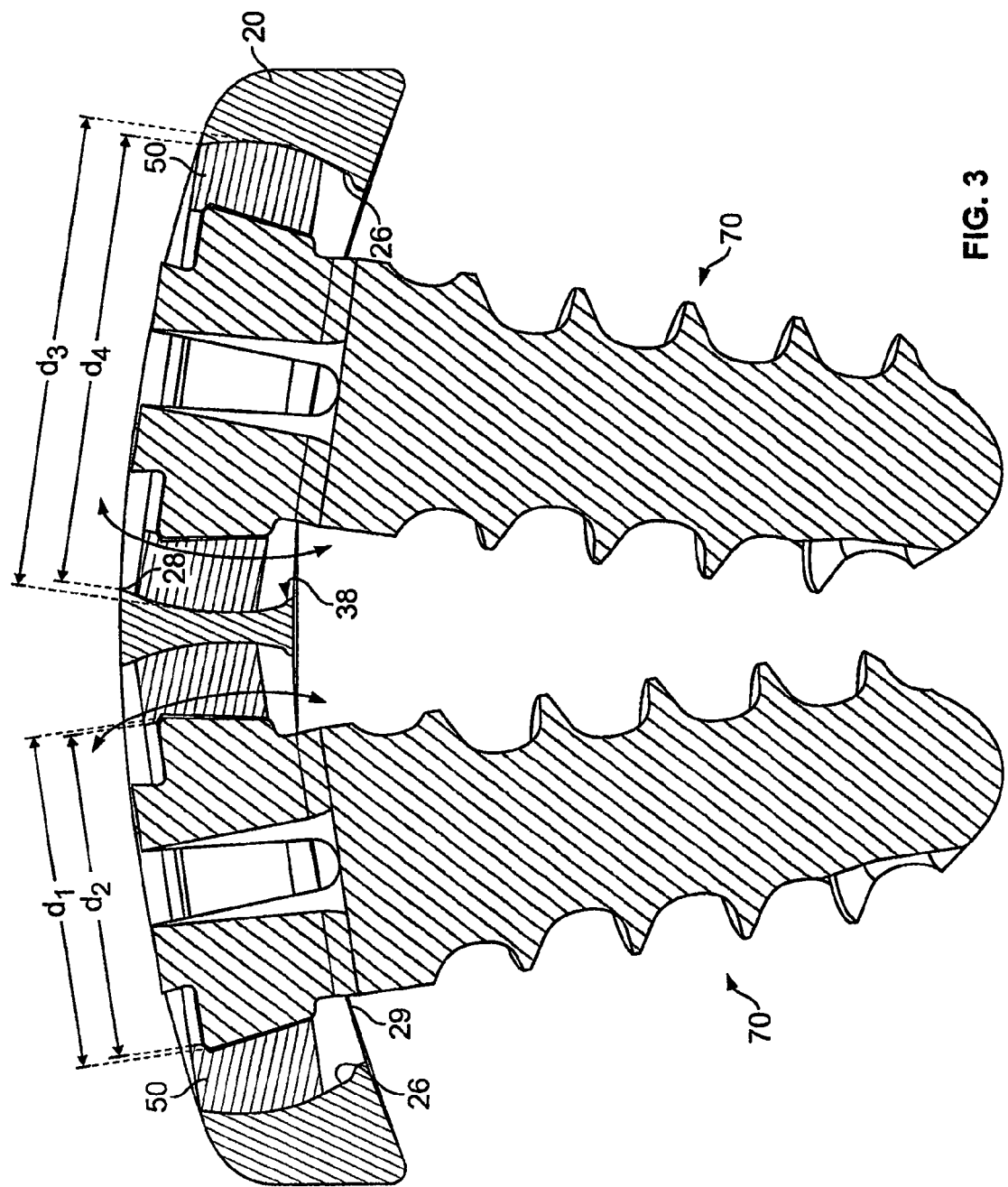
FIG. 3 is a cross-sectional end view of the bone plate system of FIG. 2 taken along line 3-3 thereof.

As is clear in FIG. 3, when the plate member 20 is secured to bone 7 by the bone screws 70, the pivot base 50 will be able to pivot within the throughbore 22, but will not be able to reach the configuration shown in FIG. 7B whereby the base member 50 may be removed from the throughbore 22. Thus, with the bone anchors 70 driven into bone 7, there is minimal risk that the pivot base 50 could be removed from the throughbore 22 either by force or geometric configuration, as a diameter $d_4$ at the upper rim portion 29 is smaller than a maximum outer diameter $d_3$ of the pivot member 50.

Figure 4:
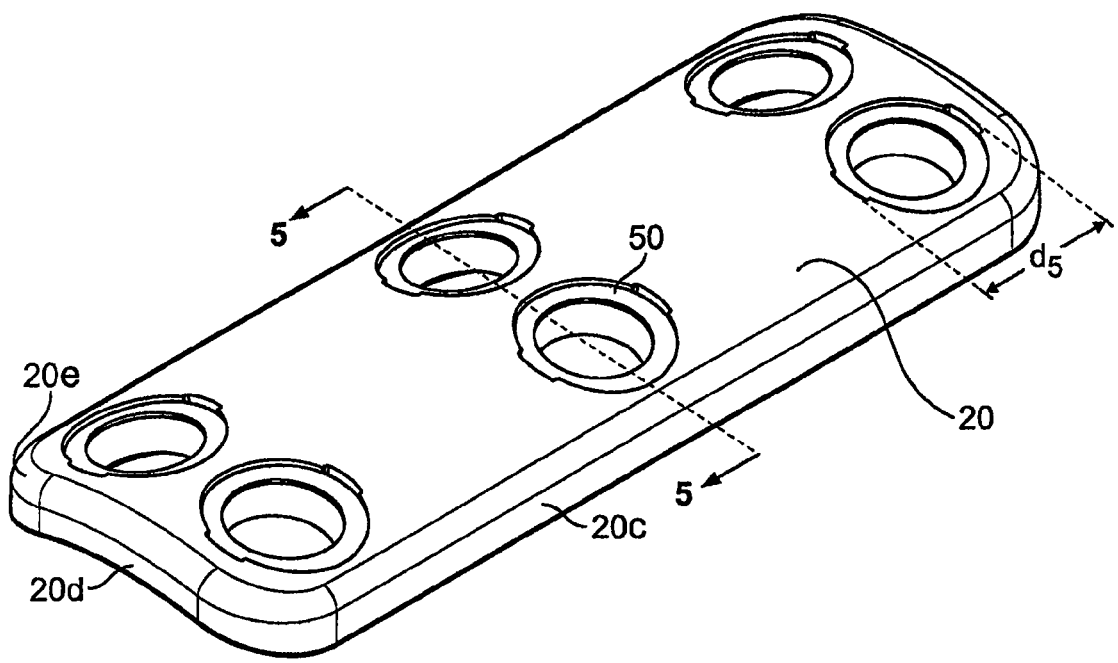
FIG. 4 is a perspective view of the bone plate system of FIG. 2 with the bone anchors removed.
Figure 5:
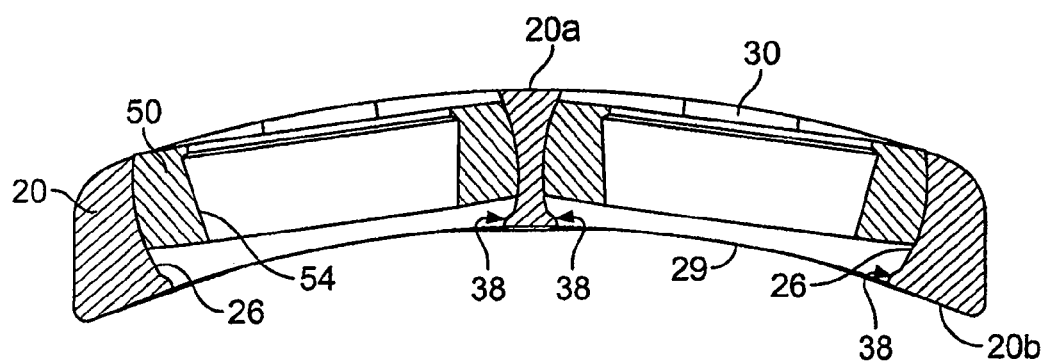
FIG. 5 is a cross-sectional end view of the bone plate system of FIG. 4 taken along line 5-5 thereof.
Figure 6:
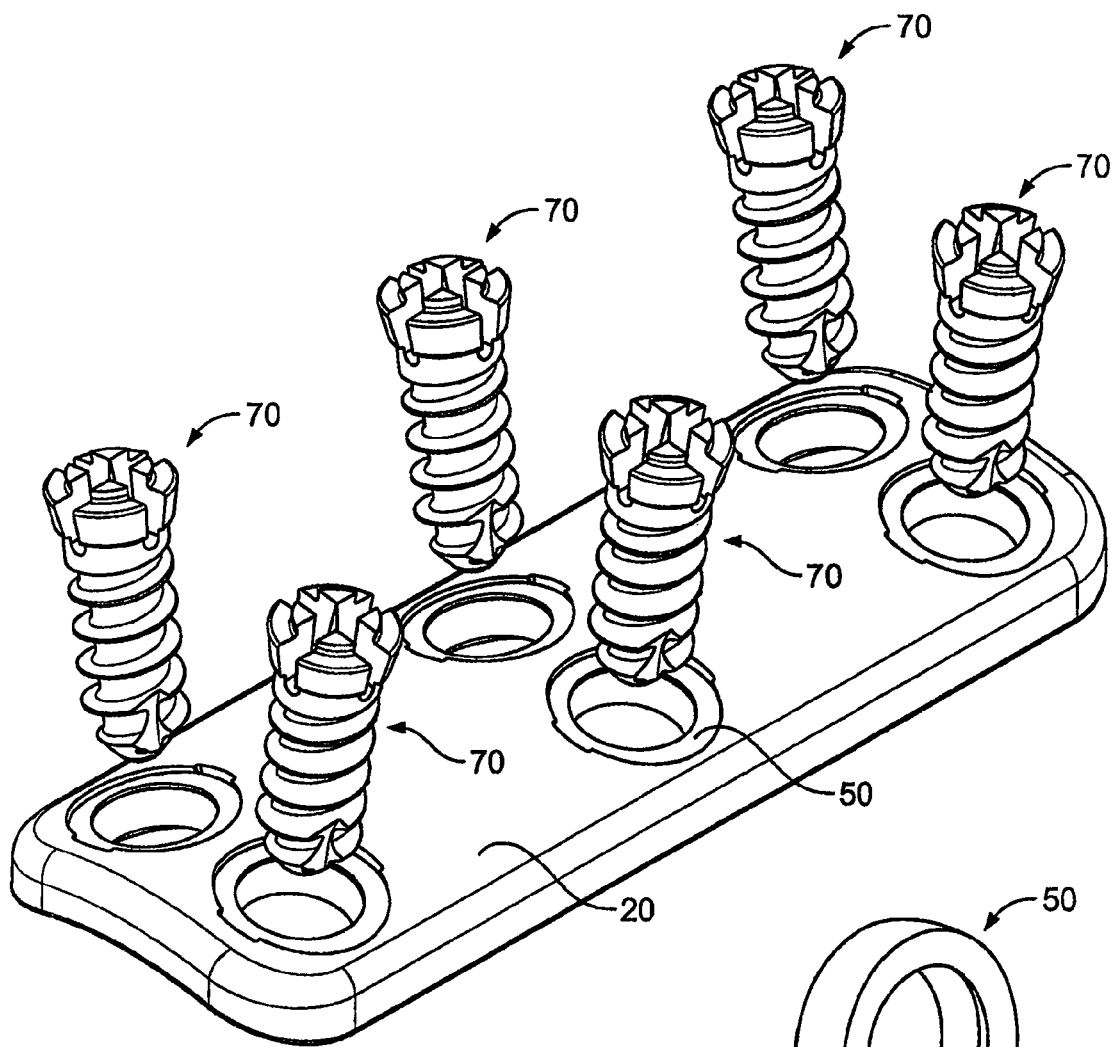
FIG. 6 is a perspective view of the bone plate system of FIG. 2 with the bone anchors exploded.

In a preferred form, the surgeon or clinician would receive the plate 20 prior to surgery with the spherical pivot bases 50 already seated within the throughbores 22 (as shown in FIG. 4) during the manufacturing and/or packaging process, but it will be appreciated that the pivot bases 50 may be installed within the throughbores 22 at another time prior to securing the plate member 20 to bone 7 with bone screws 70.

Each generally spherical pivot base 50 preferably defines an opening 52 featuring a sloped inner surface 54. The curved outer profile 56 of the pivot base 50 complements curved inner surface 26 of the throughbores 22 of the plate member 20. The bone plate system 10 may be secured to vertebrae 7 by bone anchors in the form of bone screws 70, resulting in the configuration shown in FIG. 1. In a preferred form shown in FIG. 5, the curved surface 26 of the throughbore 22 defines a generally spherical pocket, and the curved profile or surface 56 of the generally spherical pivot base 50 is shaped to be complimentary to this pocket shape, allowing the pivot base 50 to be rolled or rotated within the throughbore 22 much like a sphere within a spherical pocket, thus allowing the pivot base 50 to pivot relative to the plate 20 about all three of the primary axes, primary axes denoting the three mutually perpendicular axes of Cartesian three-dimensional space.

Before the plate member 20 is secured to the spine 6 by the bone screws 70, the spherical pivot base 50 is free to rotate within the generally spherical pocket about the central axis of the throughbore 22. In this way, when the screws 70 are installed and the patient attempts to turn his or her neck or partially rotate his or her vertebrae 7 relative to one another, the pivot bases 50 will be fixed to the screws 70 but may allow some rotational motion within the throughbore 22 relative to the plate member 20. In such a case, the bone plate 20 will impart a degree of torsional resistance to limit spinal mobility, and based on the structural, mechanical, and material characteristics of the bone plate 20, relative motion between the coupled vertebrae 7 may be effectively eliminated with the plate 20 secured thereto.

Figure 11:
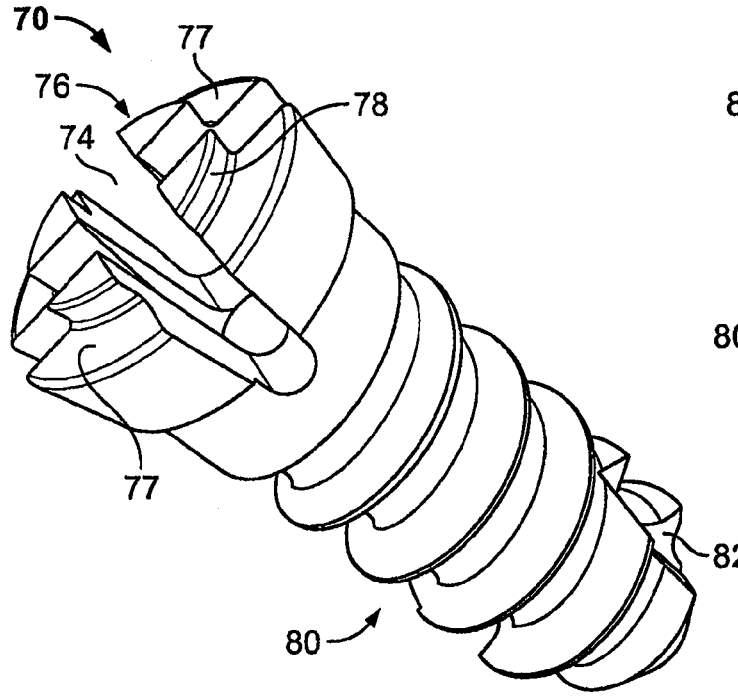
FIG. 11 is a perspective view of a bone anchor of the bone plate system of FIG. 2.
Figure 12:
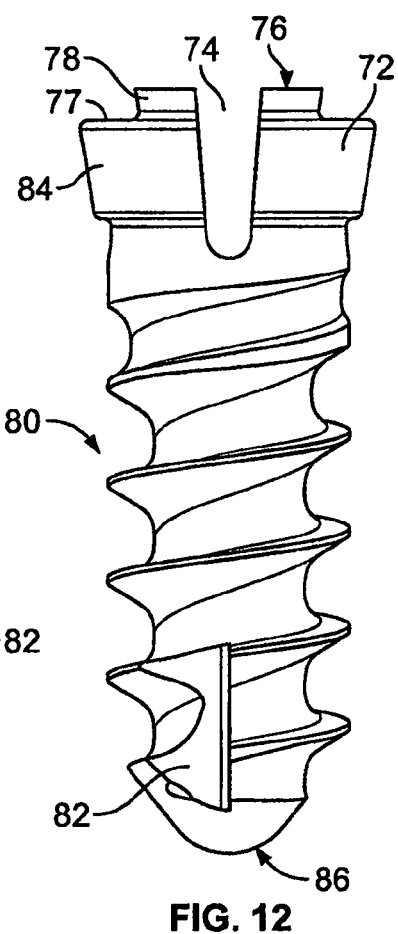
FIG. 12 is a side view of the bone anchor of FIG. 11.
Figure 13:
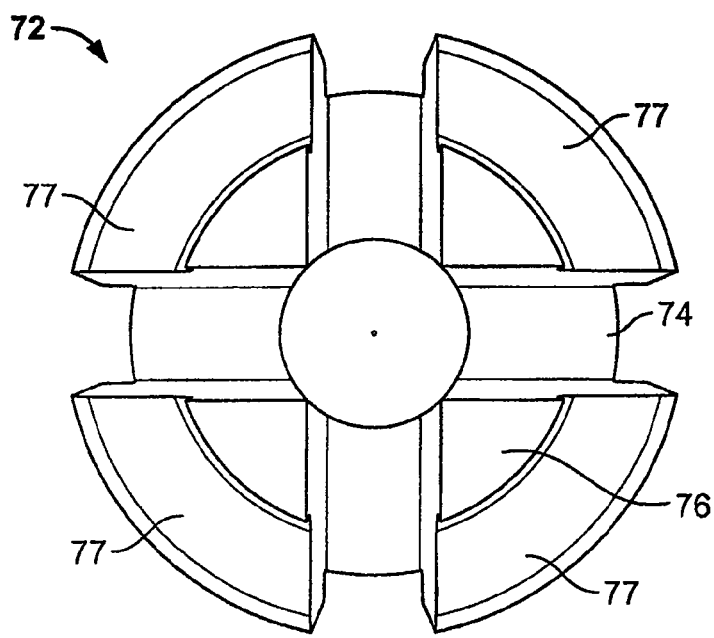
FIG. 13 is a top view of the bone anchor of FIG. 11.

Referring now to FIGS. 11-13, the bone screw 70 features a partially collapsible or compressible head portion 72 having driver engagement slots 74, bone screw retention surfaces 77, and compression jaw engagement portions 76 which are actuated by a surgical instrument 910 that contacts compression jaw engagement surfaces 78. The bone screw 70 also comprises a threaded shank portion 80, which may feature a fluted portion 82 to aid in the removal of bone chips as the bone 7 is cut. In this exemplary form, the bone screw 70 also comprises a rounded tip 86, which is characteristic of a self-tapping screw, but it should be noted that a sharper-tipped self-boring screw or any other screw design which employs the compressible head 72 may be used, as well. The bone screw 70 also features a sloped outer surface 84 which is preferably complimentary to the slopped inner surface 54 of the pivot base 50. This angled surface inhibits the head portion 72 of the bone screw 70 from driven beyond a predetermined depth relative to the pivot base 50. With a three-tiered bone plate system such as the present standard bone plate system 10, the central tier 9b bone screws 70 are typically installed generally perpendicular to the face of the bone 7, and the top tier 9a and bottom tier 9c bone screws 70 are often installed at diverging angles, further compressing the coupled vertebrae 7. As the vertebrae 7 shift and settle during the recovery period, the diverging angles tend to relax.

To prevent the bone screw 70 from backing out of the bone 7 after installation, the pivot base 50 comprises a bone anchor retention lip 58 which contacts the retention surfaces 77 of the bone screw head portion 72 with a retention contact surface 59 of the retention lip 58. The surgical tool 910 is configured to compress the screw head 72 in a preferably radial manner which reduces the largest outer diameter of the screw head 72 such that the entire head portion 72 may enter into the opening 52 of the pivot base 50 and clear the retention lip 58 without necessitating contact between the bone screw 70 and the retention lip 58. In a preferred form, the compression of the head end 72 causes only elastic stress and the head portion 72 at least partially reexpands or returns to an uncompressed configuration when released within the opening 52 of the pivot base 50, but it will, of course, be appreciated that other forms are possible wherein a combination of elastic and plastic stress is created during the compression of head 72.

With the bone screw 70 installed in a manner satisfactory to the surgeon, the surgical tool 910 may release the jaw engagement portions 76, allowing the head portion 72 to expand to form contact between the sloped outer surface 84 of the bone screw 70 and the sloped inner surface 54 of the pivot base 50. Upon release, the expansion of the screw head 72 will cause the head end 72 to be retained within the opening 52 as defined by the sloped surface 54 and the retention lip 58. In this way, the bone screw 70 will be prevented from backing out of the bone 7 because the bone anchor retention lip 58 will keep the bone anchor head end 72 secured within the pivot base opening 52 when the instrument 910 has released the bone screw head 72 and allowed the head portion 72 to reexpand, causing a largest outer diameter $d_1$ of the bone anchor head portion 72 to be larger than an entry diameter $d_2$ of the base member 50. In this manner, the present invention provides an effective and reliable apparatus which inhibits the bone anchors 70 from backing out of bone 7 wherein threaded shank portions 80 of the bone screws 70 are secured. At the same time, this method whereby the bone screw 70 is retained offers minimal probability of failure and minimal risk for the pivot bases 50 or the bone screws 70 to come out of the plate member 20 while properly installed during the recovery period.

It should further be noted that in a preferred form, the retention surfaces 77 of the bone screw 70 and the retention contact surface 59 of the retention lip 58 of the pivot base 50 are configured such that a load wherein the bone screw 70 is pushed toward the retention lip 58 will not compress the head portion 72 and allow the bone screw 70 to back out of the opening 52 of the pivot base 50. Thus, the substantially rigid pivot bases 50 are prevented from being removed from the substantially rigid bone plate 20 by virtue of the interfering dimensions therebetween, and the bone anchors 70 may not be removed from the pivot bases 50 without the aid of a specialized bone anchor driving apparatus such as the surgical tool or driver 910.

Referring now to FIGS. 34-38, a surgical tool or bone anchor driving apparatus is shown in the form of the driver 910. In a preferred form, the driver 910 comprises a jeweler's knob 922 which is connected to a handle portion 920 by a thrust bearing (not shown). The handle is connected to a shaft 960, and in a preferred form the shaft 960 is fabricated as a single piece comprising a handle engagement portion 962, a cam engagement portion 964, a concentric portion 966, and a screw head engagement cross 968. The cam engagement portion 964 of the shaft 960 is pinned to a compression shaft actuation lever or toggle-action cam lock 930 by a pin 980. As shown in FIGS. 36, 37, the lever 930 preferably features a grip portion 932, a relaxed or retraction engagement cam surface 934, and a compression or advancement engagement cam surface 936. Also in a preferred form, the concentric portion 966 of the shaft 960 is generally housed within and is generally concentric with a compression shaft or sleeve 940. The compression shaft 940 may feature a plurality of apertures 946 which offer a partial view of the concentric portion 966 of the shaft 960.

As seen in FIGS. 41 and 42, housed at least partially within the compression shaft 940 and at least partially retained by the engagement cross 968 is a compression jaw 950. To assemble the driver 910, the compression jaw 950 is first joined to shaft 960 such as by laser welding or the like. The compression shaft 940 is then slid over the compression jaw 950 and onto the shaft 960. An engagement portion 956 of the compression jaw 950 is formed to engage the engagement portion 76 of the bone screw head portion 72. The driver 910 may further feature a biasing member (not shown) such as a spring housed between the compression shaft 940 and the concentric portion 966 of the central shaft 960 to bias the compression shaft 940 toward the handle 920 with the lever or cam lock 930 moved to the relaxed or compression shaft retraction orientation shown in FIG. 36. Alternatively, the compression jaw 950 may by itself produce a biasing load sufficient to bias the compression shaft 940 toward the handle portion 920 with the lever or cam lock 930 moved to the relaxed or retraction orientation shown in FIG. 36.

Figure 34:
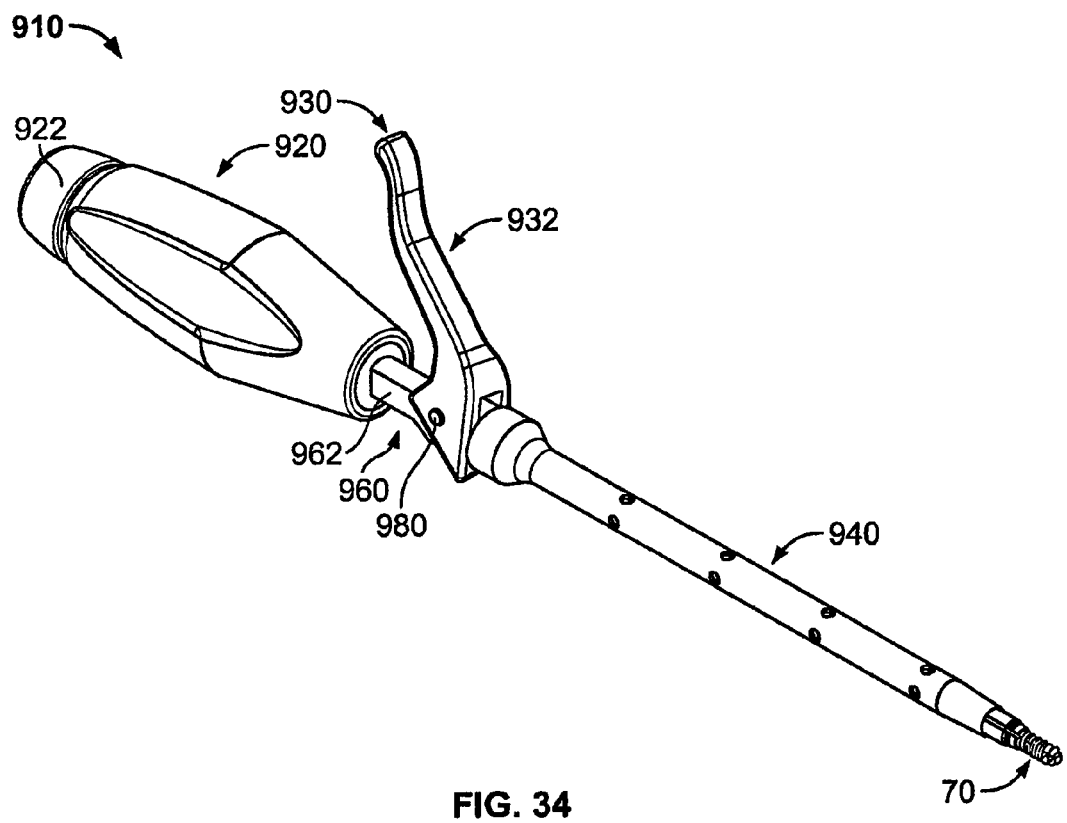
FIG. 34 is a perspective view of a driver for driving bone anchors into bone, the driver having a bone anchor attached thereto and the driver embodying features in accordance with another aspect of the present invention.
Figure 35:
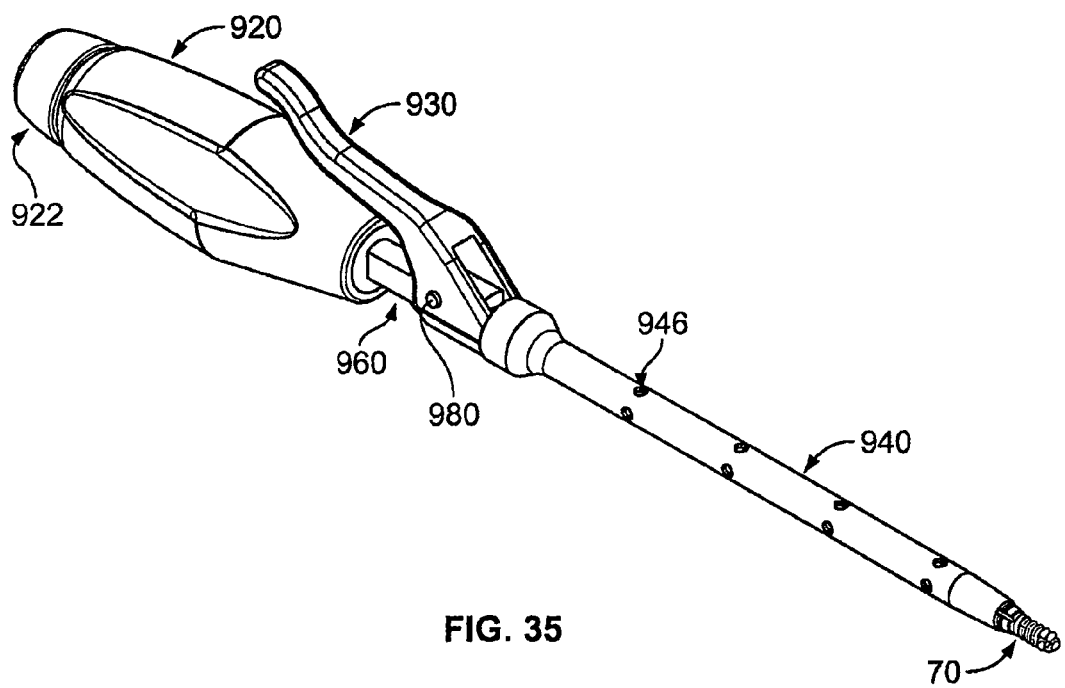
FIG. 35 is a perspective view of the driver of FIG. 34 with the compression sleeve advanced and the compression jaw and bone anchor head portion compressed.
Figures 38, 39, 40:
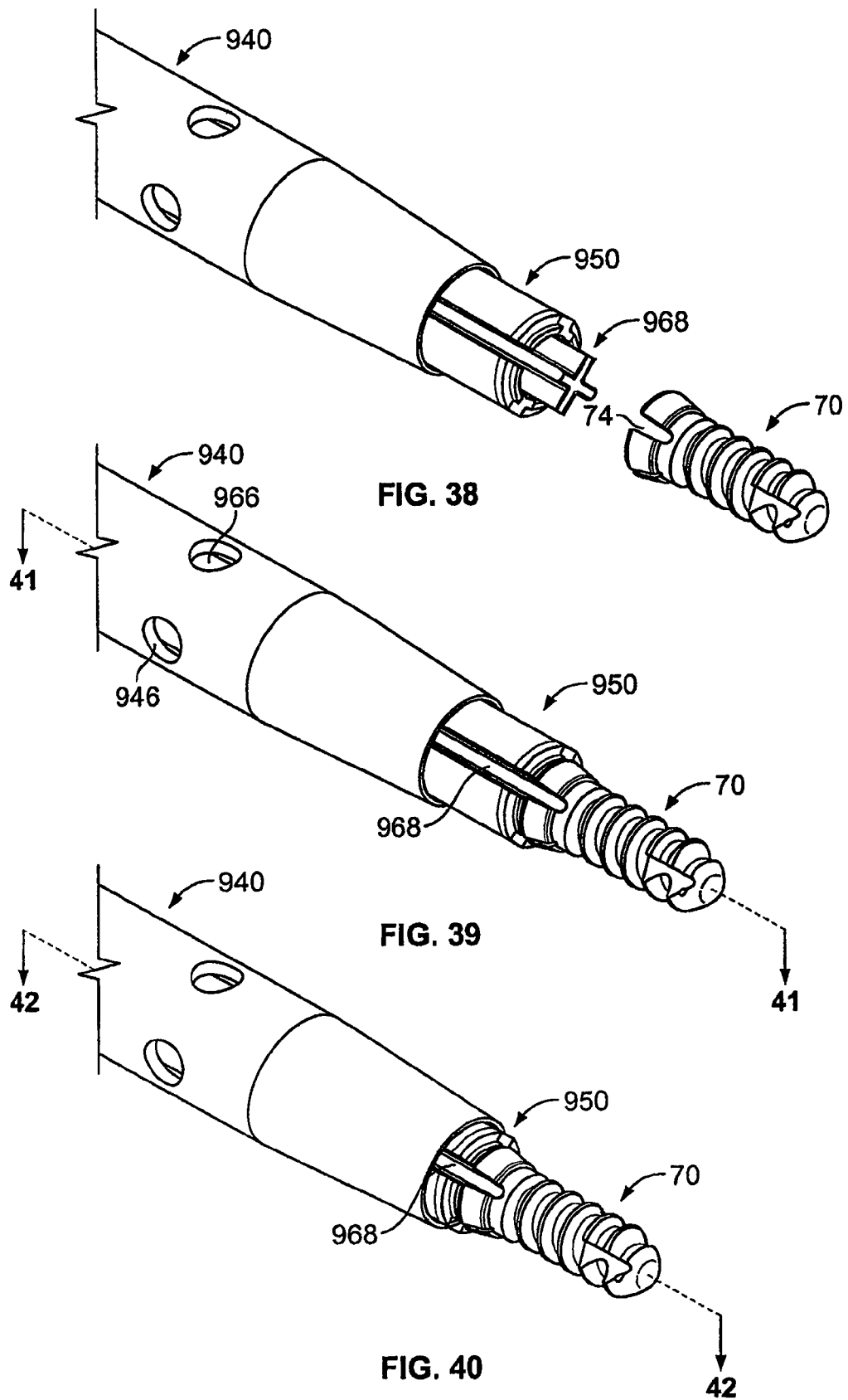
FIG. 38 is a perspective view of a portion of the driver of FIG. 34 with the bone anchor exploded therefrom.
FIG. 39 is a perspective view of a portion of the driver and the bone anchor of FIG. 34.
FIG. 40 is a perspective view of a portion of the driver and the bone anchor of FIG. 35.

In a preferred form, a surgeon or clinician would engage the bone screw with the driver 910 as it appears in FIG. 34. The engagement cross 968 engages the driver engagement ridges 74 of the bone screw 70, and the compression jaw 950 surrounds the compression jaw engagement portions 76. At this point, the surgeon may use the grip portion 932 to toggle the switch 930 to the compression position seen in FIG. 35. By actuating the cam lock 930, the lever 930 transitions from abutting the compression sleeve 940 with the relaxed or retention cam surface 934 to abutting the compression sleeve 940 with the compression or advancement cam surface 936, and thus the cam lock 930 causes the compression sleeve 940 to translate down the shaft 960, compressing the jaw 950 and causing the engagement portion 956 to compress the resilient screw head portion 72.

The knob 922 and the handle 920 are preferably linked by a thrust bearing (not shown) allowing the knob 922 to remain stationary relative to the handle 920 as the handle 920 and shaft rotate in kind with one another. The shaft 960 is connected to the handle 920 such that as the handle 920 is rotated, the shaft 960 rotates, as well. In this way, the surgeon may hold the jeweler's knob 922 in the palm of his or her hand and rotate the handle 920 with his or her fingers. Thus, the screw 70 is connected to the engagement cross 968, the cam lock 930 is transitioned to the advancement orientation seen in FIG. 37, causing the compression sleeve 940 to translate and compress the jaw member 950, compressing the resilient bone screw head 72. This configuration also aids the surgeon because the compression member 950 acts to retain the bone screw 70 to the driver 910 such that the bone screw 70 and driver 910 may together be moved over the surgical site and directed toward the bone anchor insertion point with minimal risk that the bone screw 70 will come out of engagement with the driver 910. Thus, the jaw 950 serves to temporarily secure the bone anchor 70 to the driver 910, as a conventional driver may rely on solely engaging the engagement slots 74 which could either be ineffective in securing the bone screw 70 to the driver or engage the bone screw 70 effectively filling the engagement slots 74 such that the bone screw head portion 72 could not be compressed to clear the bone anchor retention member 58 and enter the pivot base opening 52. The present driver 910 is preferably configured such that the engagement cross portion 968 may create sufficient torque to drive the bone anchor 70 but leave space to allow the bone screw head portion 72 to be compressed, utilizing the jaw 950 not only to compress the screw head 72 but to aid in retaining the bone screws 70 to the driver 910.

The surgeon may install the bone screw 70 into bone 7 in any desired orientation within a range of permissible orientations allowed by the plate member 20 and the pivot base 50. The compression of the bone screw head end 72 by the compression jaw 950 preferably allows the bone anchor member 70 to clear and pass by the head portion retention lip 58, and with the bone screw 70 is in a seated configuration, the cam lever 930 may be toggled to the retraction position to allow the resilient screw head 72 to at least partially reexpand within the pivot base opening 52. This toggle action causes the compression shaft or sleeve 940 to translate relative to the central shaft member 960 once more as the compression shaft 940 returns to the configuration shown in FIG. 34, loosening the grip of the jaw 950 on the engagement portion 76 of the bone screw 70. With the jaw engagement portion 76 of the bone screw 70 released from the jaw member 950, the bone screw head portion 72 reexpands to be constrained within the opening 52 of the pivot base 50 and the instrument 910 may be moved away from the bone screw 70 and cleared of the surgical site.

It should be noted that the plate member 20 and any other bone plate member in accordance with the present invention may feature a plurality of bone pin holes (not shown) for inserting bone pins (not shown) into bone for temporarily restraining the bone plate in a desired location and orientation prior to driving bone anchors into bone to secure the plate member thereto. The bone pin holes may be placed at opposite and/or diagonal ends of the bone plate.

It should further be noted that in the event that the bone is stripped or chips during installation of the bone screws, a rescue screw (not shown) may be provided for securing the plate member to bone. A rescue screw is a screw that has a larger thread diameter, or a larger central or minor diameter, or both relative to conventional bone screws when secured within bone. The larger dimensions create a degree of interference with the bone and as such, the rescue screw is able to gain purchase in a stripped hole, treating the hole as if it were merely a pilot hole because of the larger size of the rescue screw.

Turning now to FIGS. 14-18, another embodiment having features according to the present invention is shown. For the purpose of brevity, discussion pertaining to this and subsequent embodiments will be discussed primarily in light of how the embodiments differ from the bone plate system 10 shown in FIGS. 1-8. Preferably, the surgical instrument 910 is configured for use with all bone plate system embodiments and pivot base concepts that are shown for exemplary purposes herein.

Figure 14:
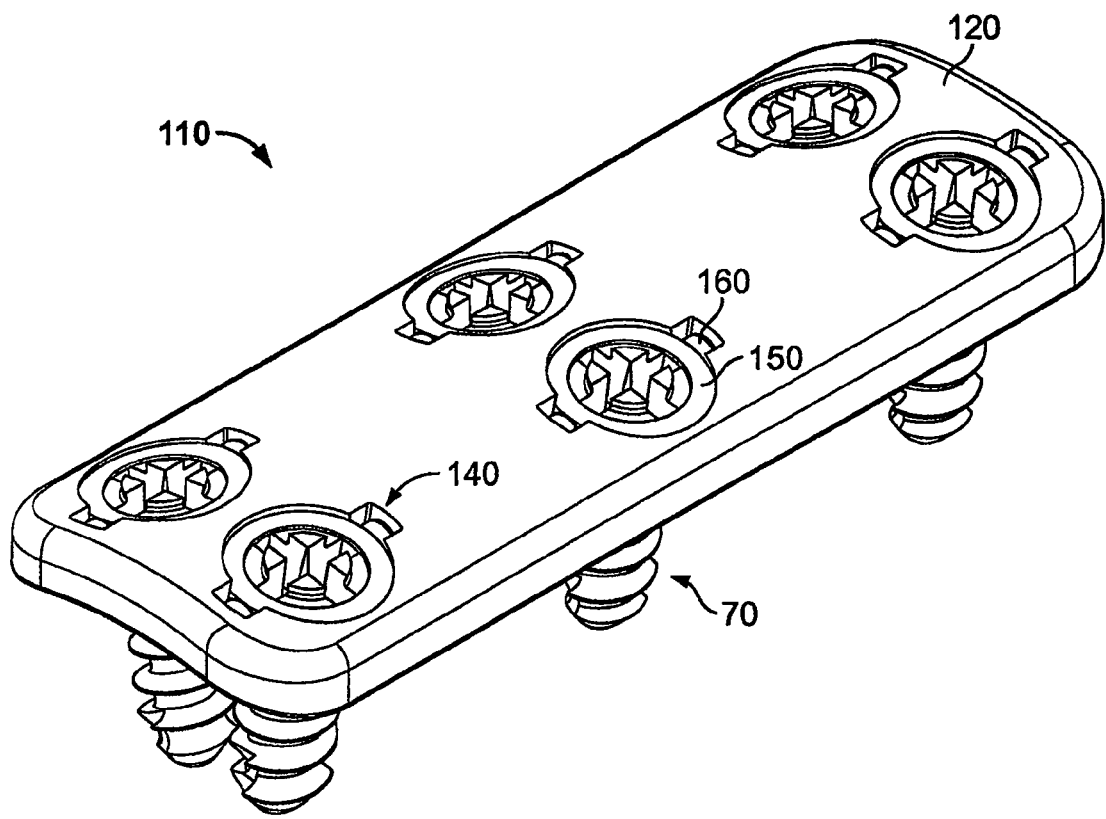
FIG. 14 is a perspective view of another bone plate system embodying features in accordance with the present invention.
Figure 15:
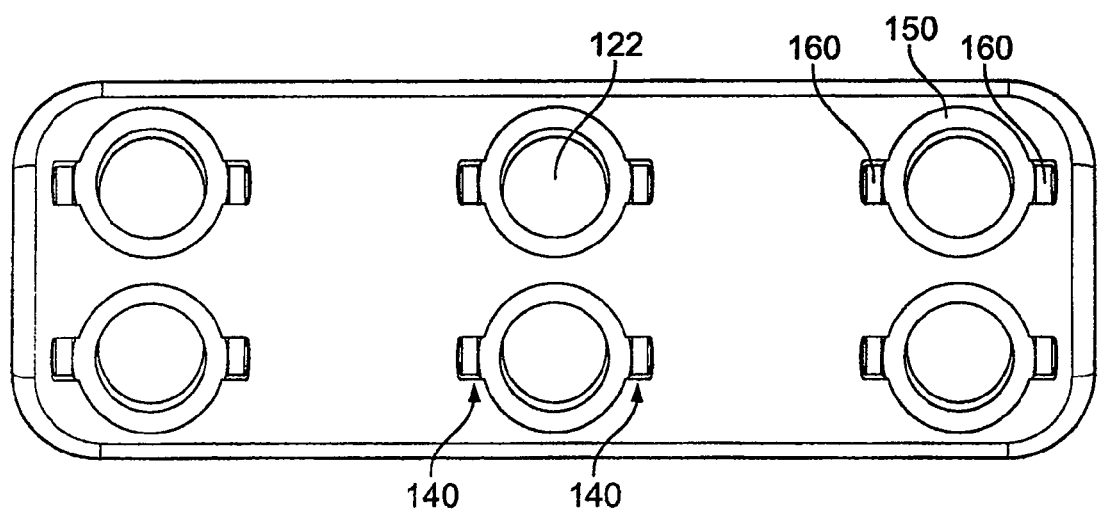
FIG. 15 is a top view of the bone plate system of FIG. 14 with bone anchors removed.
Figure 16:
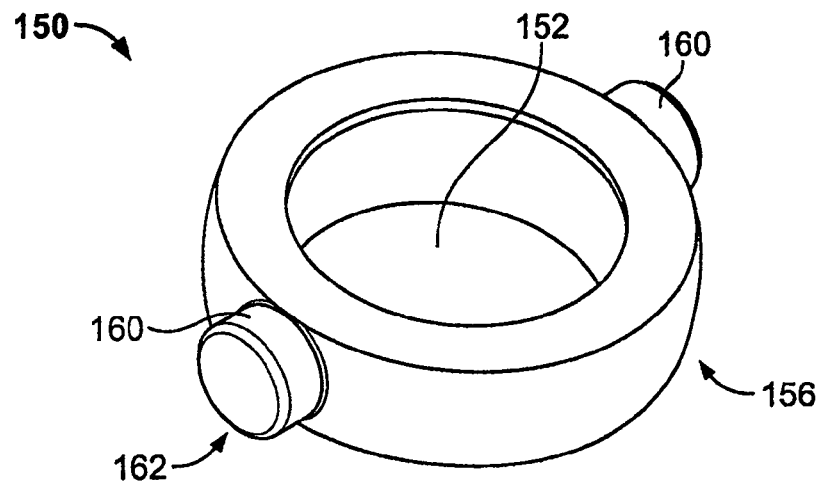
FIG. 16 is a perspective view of a pivot base of the bone plate system of FIG. 14.
Figure 17:
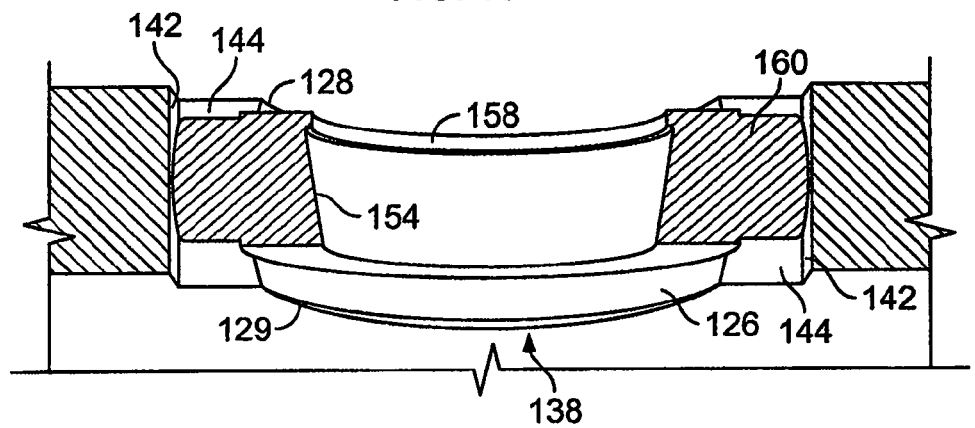
FIG. 17 is a cross-sectional side view of a portion of the bone plate system of FIG. 14.
Figure 18:
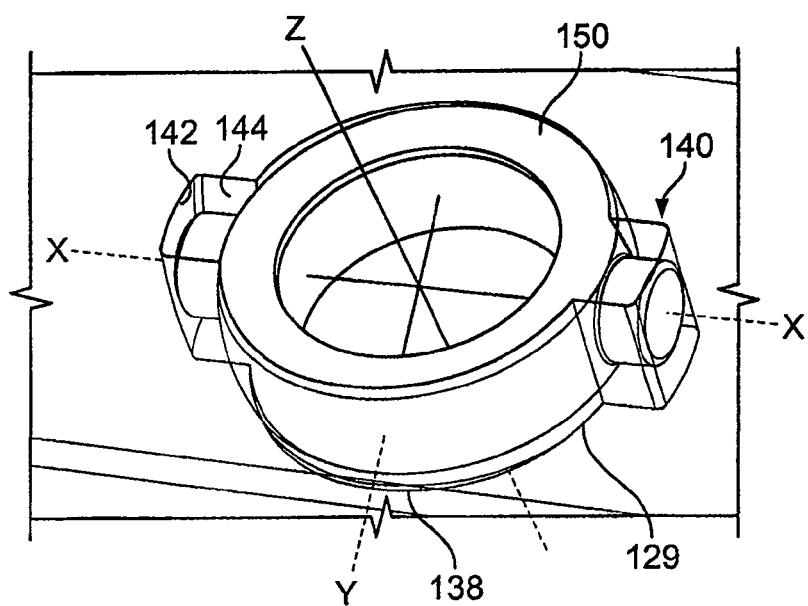
FIG. 18 is a perspective view of a portion of the bone plate system of FIG. 14 wherein the plate has been represented as transparent for the purpose of showing detail.

FIG. 14 shows a bone plate system 110 comprising a bone plate 120, which is similar in many respects to the plate 20 discussed previously with the exception that the plate member 120 features pivot bases 150 with protrusions or extended members in the form of pegs or posts 160. The pivot bases 150 are configured to be recieved within throughbores 122 and the pegs 160 are configured to fit within peg access slots 140 adjoined to the main throughbore portion 122. The post insertion cavities 140 have an end wall that is preferably substantially vertical with a curved profile as seen in FIGS. 17, 18 and extended side walls 144 that serve to limit and provide additional control over the pivotal motion of the pivot base 150, giving the pivot base 150 the ability to pivot or rotate with respect to only two of the three primary axes or, in other words, restricting the ability to pivot or rotate with respect to one of the three primary axes.

The pivot bases 150 feature an opening 152 through which a bone screw 70 may pass in much the same manner described above with respect to the pivot base 50 of the previously discussed bone plate system 10. The extended members 160 are in general alignment with the longitudinal axis of the plate 120 and, in a preferred form, inhibit the pivot base 150 from rotating about the central axis of the throughbore 122. This is in contrast to the previous bone plate system 10 discussed above in which the pivot bases 50 are free to rotate about the central axis of the throughbores 22 until the bone screw 70 is driven into bone 7 and seated with the screw head portion 72 is allowed to expand within the opening 52 and form a tight fit between the complimentary sloped surfaces 54, 84 of the pivot base 50 and bone screw 70, respectively. It should be noted that features that are similar to features of the previously discussed bone plate system 10 may be denoted in a similar manner, such as throughbores 22 and 122 and pivot bases 50 and 150.

In addition to inhibiting the pivot base 150 from rotating about the central axis of the throughbore 122, the posts 160 also limit the range through which the pivot bases 150 may pivot fore and aft relative to the longitudinal axis of the plate member 120. The pivot base 150 is more limited in this range of motion relative to the pivot base 50 because a post member 160 on one side of the base member 150 will contact the bone and inhibit further pivoting in that angular direction.

Should the vertebrae 7 shift or move closer to each other during the recovery period, the extended members 160 may limit the amount that the screw 70 and pivot base 150 may pivot relative to the plate 120. In addition, the pegs 160 also allow the system 110 to impart more torsional resistance to inhibit movement of the coupled vertebrae. The plate 120 will impart some resistance when the patient attempts to move the coupled vertebrae relative to one another, but the pegs 160 further hinder this motion. The previously discussed system 10 featured spherical pivot bases 50 that did not have pegs or posts, and in this way the pivot base 50 could rotate slightly about the central axis of the throughbore 22. The system 110 featuring the generally spherical pivot base 150 with projecting members 160 will not allow such rotation about the central axis of the throughbore 122, and as such the system 120 will provide more substantial torsional resistance to attempted movement of the coupled vertebrae. This mechanical characteristic will be discussed in greater detail below as it relates to monoplate (single-row or single screw per vertebral level as opposed to double-row or dual screws per level) embodiments of the present invention.

Just as the pivot base 50 features a curved outer profile 56, the present pivot base 150 also features a curved outer profile 156 which is complementary to a curved inner surface 126 of the throughbore 122. The throughbore 122 also features an upper edge portion 128 and a lower edge portion 129. The preferably spherical complementary surfaces 126, 156 allow the pivot base 150 to pivot within the throughbore 122 about the two primary axes not constrained by the extended members 160. In this way, the pivot base 150 is free to pivot about the longitudinal axes of the posts 160, with the extended members 160 acting as pivot members and the surface 156 articulating relative to the inner surface 126 of the throughbore 122, this pivotal motion being limited by at least one pivot base retention lip 138 near the lower edge portion 129 of the throughbore 122. Should the pivot base 150 pivot to a predetermined limit, the base 150 will contact the retention lip 138, which will inhibit further pivoting in that particular direction. The pivot base 150 is also free to pivot such that one of the pegs 160 moves up relative to the bone 7 120 while the other moves down relative to the bone 7, this motion being inhibited should a peg member 160 pivot into contact with a bone 7 or the pivot base 150 contact a retention lip 138. The pivot base 150 could also pivot both fore and aft and side to side with respect to the longitudinal axis of the plate member 20 at the same time. Regardless, the pivot base 150 preferably does not rotate about the central axis of the throughbore 122 beyond a predetermined amount of play provided within the peg slots 140. In a preferred embodiment, very little to no play is provided between the posts 160 and the side walls 144 of the post access grooves 140, but it is, of course, possible that in alternative embodiments a larger predetermined range of play may be allowed.

As seen in FIG. 17, the pivot base 150 also features slightly rounded surfaces 162 at the ends of the extended members or posts 160. The surfaces 162 allow for the pivoting motion whereby the pegs 160 may contact the bone 7, and an end surface 142 of the access cavity 140 is generally vertical with respect to the central axis of the throughbore 122, but features a curved profile the account for the curvature of the ends 162 of the extended member 160 and allow relative motion thereby. To install the spherical pivot base 150 with pivot members 160 into the throughbore 122 and adjoining access slots 140, the pivot base 150 is installed using a method similar to the method whereby pivot bases 50 are installed within throughbores 22 in the system 10 discussed above. As shown in FIGS. 18A-D, the pivot base 150 is slidably inserted or translated into the throughbore 122 such that the posts 160 are slidably inserted into the slots 140 with the orientation of the pivot base 150 preferably approximately perpendicular to the orientation seen in FIG. 14. Next, the pivot base 150 may be rolled or rotated into a seated orientation. As with the previous bone plate system 10, seating the pivot base 150 requires that the pivot base 150 be forced to overcome interference between the pivot base 150 and the retention lip 138 of the throughbore 122, preferably causing only elastic stress to the retention lip 138 and/or pivot base 150. This configuration will inhibit the spherical pivot base 150 from pivoting beyond a predetermined range while properly seating and securing the pivot base 150 within the throughbore 122 by virtue of the rigidity of the plate member 120 and the pivot base 150 and the interfering spherical geometry and dimensions therebetween. In a preferred form, the minimum design load required to force the pivot base 150 past the lip 138 will be greater than the maximum load that the lip 138 and pivot base 150 are predicted to be subjected to under any other expected conditions during the recovery period.

Turning now to FIGS. 19-22, another embodiment according to the present invention is shown in the form of a standard or non-dynamized bone plate system 210. The present system 210 preferably utilizes the same pivot bases 150 and bone screws 70 as the previously discussed system 110 and is used in much the same manner as the previous system 110. Furthermore, the pivot bases 150 are preferably installed in the same manner and must be forced past at least one retainment lip 238 featured within a throughbore 222. The present bone plate system 210, however, may offer several advantages that are a result of the utilization of a bone plate 220, which offers similar structural performance and mechanical characteristics to the previous plate member 120, but includes apertures 232, end impressions 233, and side impressions 234. The impressions 233, 234 allow the surgeon to view more of the spine 6, and the apertures 232 offer the ability to view more of the spinal discs 8 or bones 7 during surgery. This enhanced view of the surgical site may allow a surgeon greater ability to choose optimal placement for the plate member 220 and may also allow a surgeon to view areas of a fusion or graft site, intervertebral space, or spinal injury in an advantageous manner. In addition, the apertures 232 may also allow a surgeon or clinician to perform operations within the intervertebral space using a cannula or other minimally invasive instrument extending through an aperture 232 and into the intervertebral space. Furthermore, the reduced cross-section between tiers due to the apertures 232 and side impressions 234 may cause the segments between throughbores 222 to be easier to bend should a patient require the plate member 220 to contour present or desired spinal curvature, which is advantageous because bending the bone plate 220 at the throughbores 222 could compromise the intended geometric configuration and/or mechanical characteristics of the plate member 220, the throughbores 222, and the pivot bases 150.

Though apertures and/or impressions such as the apertures 232 or impressions 233, 234 are not shown as a feature all embodiments disclosed herein for exemplary purposes, it will of course be appreciated that and/or impressions may be incorporated a features of any bone plate systems described herein or any other possible embodiments incorporating features according to the present invention.

Looking now to FIGS. 23-26, another embodiment of the present invention is shown in a monoplate or single-row bone plate system 310. The present bone plate system 310 may be referred to as monoplate as it comprises a plate 320 that features only a single screw per vertebral level. In other words, plate 320 preferably has only one set or row of throughbores 322 or one throughbore 322 per tier, not paired sets of throughbores as seen in the bone plate systems 10, 110, 210 discussed above. The monoplate system 310 also employs the pivot bases 150 comprising pegs or posts 160. As shown in FIG. 25, the monoplate 320 preferably features a curved profile similar to that of the previously discussed embodiments so that it may contour to the face of a vertebra 7.

Generally, a surgeon choosing to utilize the bone plate system 310 will install only one such system 310, and the surgeon may install the system 310 centrally with respect to the anterior cervical region of the vertebral column 6 or the present bone plate system 310 may be installed such that the plate member 320 is positioned off-of-center with respect to the midsagittal plane. Such a decision would be a factor of the individual case of the patient and the preference of the surgeon, but some surgeons may install the bone plate system 310 off-of-center to ensure that the bone plate system 310 poses minimal interference to normal swallowing motions and avoids agitating or damaging the esophagus. The curved profile of the plate 320 allows a favorable contour to the bone 7 regardless of the surgeon or clinician's preference of a centered or off-of-center placement of the bone plate system 310.

Regardless of whether the present bone plate system 310 is installed in a centered or off-of-center position, the narrower profile of the plate member 320 may allow the present system 310 to be installed with a smaller incision, which may lead to less discomfort and/or a faster recovery. Furthermore, the single-row configuration requires fewer bone anchors and thus the surgery to secure the plate member 320 to bone 7 may be less time-consuming. A smaller plate profile is also less prone to inhibit swallowing and/or impede on the esophagus and other soft tissues. The narrower plate member 320 is thus less likely to irritate the esophagus and other tissues, decreasing the probability of complications such as esophageal dysphagia or other possible side-effects known to occur as a result of the presence of an anterior cervical plate.

In general, the narrower plate member 320 will not by itself offer the torsional resistance of the wider two-rowed plate members discussed above, but the extended members 160 of the pivot bases 150 will enhance the torsional resistance of the monoplate bone plate system 310 such that relative movement of the coupled vertebrae 7 is sufficiently inhibited. The posts 160 extend between the extended straight side portions 344 of the access slots 340, thus the pivot bases 150 are inhibited from rotating about the central axes of the throughbores 322 and thus the posts 160 contacting the extended side walls 342 of the peg slots 340 will serve to add to the torsional resistance supplied by the bone plate system 310 and inhibit rotation of the secured vertebrae 7 relative to one another. Thus, the pegs 160 allow the bone plate system 310 to offer sufficient torsional stability to be used without employing less elegant methods for attempting to increase torsional stability such as bone-engaging spikes that can be pressed into the face of a bone and may damage osseous tissue.

Figure 27:
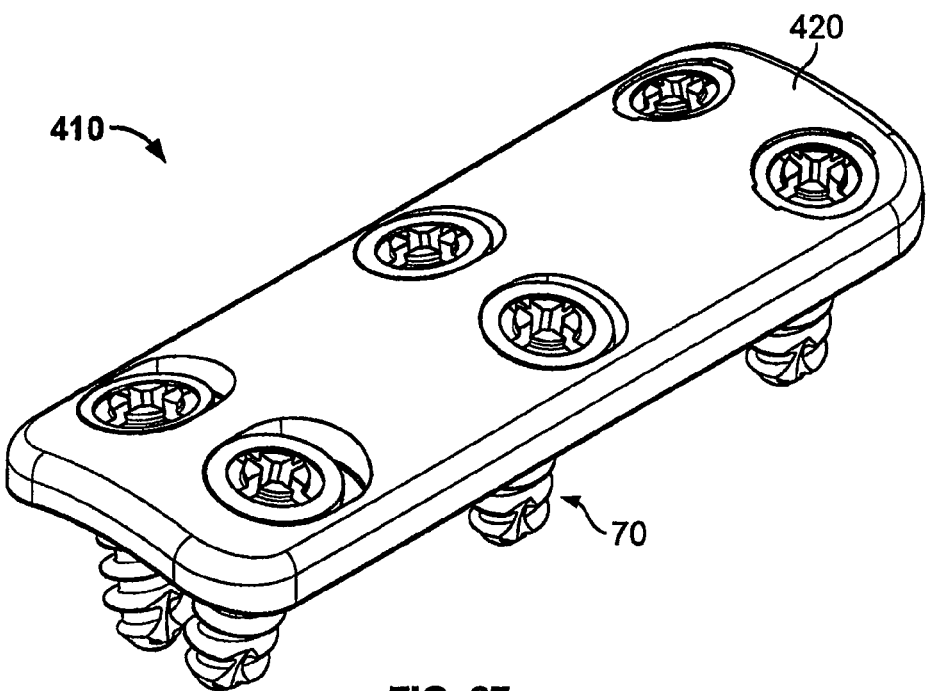
FIG. 27 is a perspective view of a bone plate system embodying features in accordance with the present invention.
Figure 28:
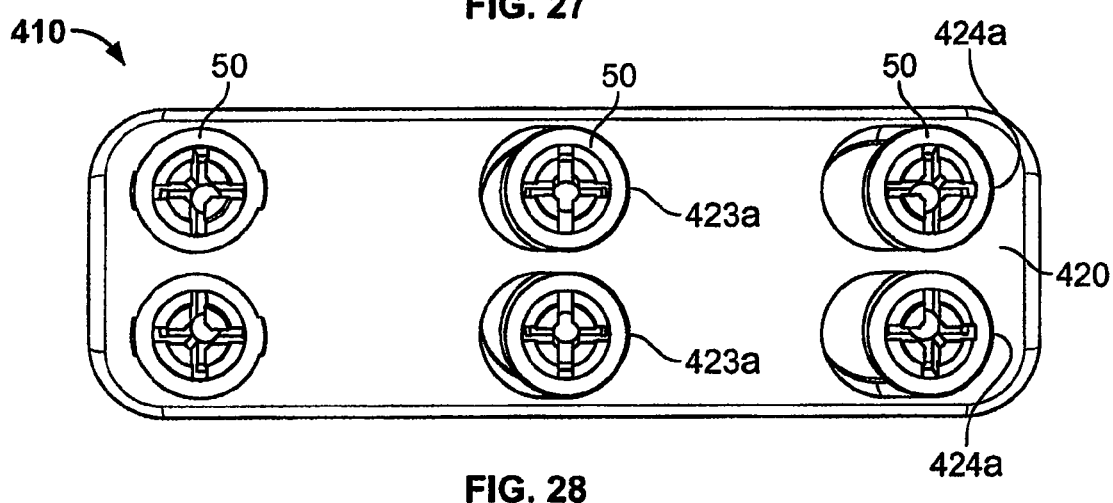
FIG. 28 is a top view of the bone plate system of FIG. 27.
Figure 29:
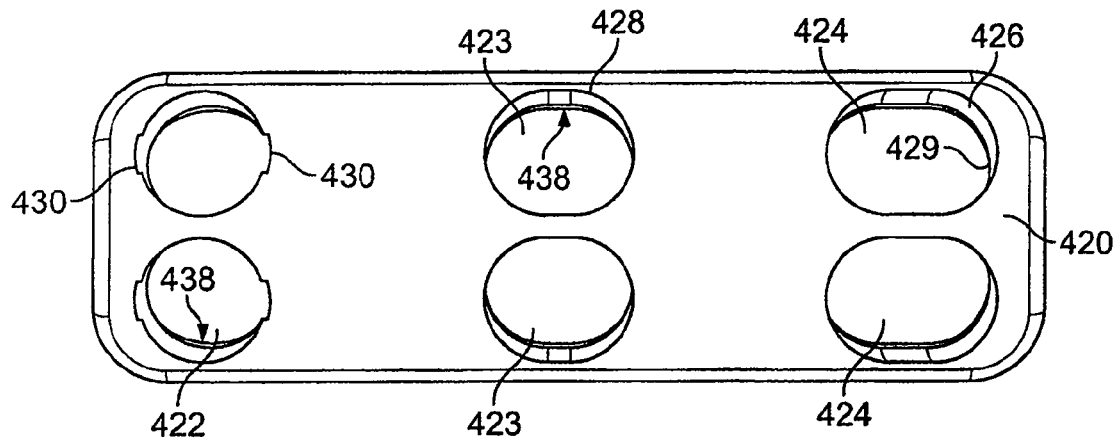
FIG. 29 is a top view of the plate of the bone plate system of FIG. 27.

Turning now to FIGS. 27-29, another embodiment according to the present invention is shown in the form of a dynamic bone plate system 410. The dynamic bone plate system 410 is similar in many respects to the previously discussed bone plate system 10 in that the present bone plate system 410 comprises a generally rectangular plate member 420, generally spherical pivot bases 50, and bone screws 70, but the present plate member 420 features both standard 422 and dynamized 423, 424 throughbores. In utilizing the dynamic system 410, the bone 7 that the surgeon desires to stabilize such as, for example, a vertebrae 7 that has been injured or features a bone graft, will be aligned with the standard throughbores 422, and the adjacent vertebra 7 will be aligned with elongated, dynamized throughbores 423. The throughbore 423 has the same width as the diameter of the generally circular through throughbore 422, but the dynamized throughbore 423 is elongated to allow the pivot base 50 to translate a predetermined distance relative to the plate 420 within the throughbore 423, and, in a preferred form, the predetermined length of translation is approximately 1.25 millimeters, though it will be appreciated that it could be any other length according to the needs of the patient or the preference of the surgeon. In a similar manner, the next vertebra 7 (one removed from the stationary throughbores 422) will be aligned with longer elongated throughbores 424 which preferably allow approximately two times the length of possible translation of the intermediate throughbores 423. The longer elongated throughbores 424 allow twice the length of translation of the intermediate elongated throughbores 423 because the longer elongated throughbores 424 account for relative motion between both the first and second and the first and third vertebra 7. Generally, the dynamized plate member 420 will be secured such that the standard throughbores 422 are aligned with the uppermost secured vertebrae 7 and the dynamized throughbores 423, 424 are aligned with the next two vertebrae 7 moving down the spine 6. Preferably, the bone anchors 70 are installed at far ends 423a, 424a within the elongate throughbores 423, 424. As the vertebrae 7 shift and/or settle during the recovery period, the bone anchors 70 within the dynamized throughbores 423, 424 generally tend to translate relative to the plate member 420 within the throughbores moving closer to the standard or non-dynamized throughbores 422.

In the same way that the second pair elongated of throughbores 424 moving away from the standard pair 42 allows twice the translation of the first pair of elongated or dynamized throughbores 423, it will be appreciated that further embodiments are possible which may feature four or even five or more pairs of throughbores. In these cases, the fourth pair of throughbores of the plate member—the third pair moving away from the standard, non-dynamized pair—would preferably allow three times the length of translation that the second pair of throughbores 423 allows and the fifth pair of throughbores would preferably allow four times the length translation that the second pair of throughbores 423 allow. Generally, a choice regarding the number of pairs of throughbores on a bone plate is dependent on the type and severity of the injury, the number of vertebrae 7 being fused, the needs of a particular patient, and/or the preferences of a surgeon or specialist.

As discussed above, vertebrae 7 may shift or move closer together during the healing, grafting, and/or fusion process. In the previously discussed embodiments, the screws 70 driven into bones 7 may pivot relative to the plate member by way of the spherical pivot bases to accommodate the relative movement of the bones 7. In the present dynamic system 410, this movement may be accounted for by both pivoting and translation. Generally, the type of bone plate system chosen—standard or dynamic—is dependent on the type and severity of the injury, the number of vertebrae being fused, the expected amount of vertebral settling, and/or the preferences of the surgeon or specialist. In some cases, a surgeon may believe that the pivoting would be sufficient to accommodate the expected degree of shifting and/or changes in curvature. In other situations, a surgeon may believe that pivoting alone may not accommodate the expected shifting and/or changes in curvature and translation of the pivot bases 50 relative to the plate may be necessary, as well. If a surgeon believes that the recovery period may entail more movement between adjacent vertebrae than pivotal motion alone could accommodate, a bone plate system employing dynamized throughbores will generally be utilized. In these cases, the pivoting capability remains quite important and may still account for a portion of the vertebral settling, but the translational capability may be of primary importance, as well.

Should a bone plate system utilizing dynamic or dynamized throughbores be selected, the surgeon may use a specific installation configuration to provide advantageous conditions under which bone growth or healing is known to take place. The dynamized bone plates system 410 shown in FIG. 28, for example, preferably has bone screws 70 spaced in the same manner that a surgeon would desire that the bone anchors be spaced immediately following securement to bone 7. As discussed previously, Wolff's Law teaches the positive effects that compression can have upon bone growth and the integrity of a graft or healed injury. Preferably, a surgeon will attempt to install the bone screws 70 in the elongated throughbores 423 and 424 such that the head portions 72 are placed at far ends 423*a*, 424*a* and are as far away from standard or non-dynamized throughbores 422 as possible while keeping all vertebrae 7 that are coupled to the bone plate 420 in compression such that the coupled vertebrae 7 will remain in compression as the region heals. The elongated throughbores 423, 424 will allow the bone screws 70 and generally spherical pivot bases 50 to have a predetermined range of pivotal and translational motion in accordance with shifts, settling, and/or changes in curvature within the vertebral column 6. During the recovery period, which generally ranges between several weeks to several months, the pivot bases 50 within the dynamized throughbores 423, 424 may translate within the throughbores 423, 424 toward the standard pair of throughbores 422 as the vertebrae 7 shift or settle.

Seating the generally spherical pivot bases 50 into the standard or non-dynamized throughbores 422 of the present plate member 420 is preferably accomplished by same the procedure described above with respect to the standard throughbores 22 of the bone plate system 10, in which the pivot bases 50 are inserted using access or insertion slots 430. In the case of the elongated throughbores 423 and 424, no notches are necessary as the pivot bases 50 may be inserted and rolled into proper seating without the presence of insertion notches such as the access notches 30 on the standard throughbores 422. The pivot bases 50, however, must still be forced past at least one retention lip 438 just as the pivot base 50 must be forced past a retainment lip 38 in the previously discussed bone plate system 10. For the elongated throughbores 423 and 424, the elongation satisfies the geometric requirements for which the access or insertion grooves 430 are provided on the standard throughbores 422, and the retention lips 438 serve to retain the pivot bases 50 within their corresponding throughbores as the pivot bases 50 are thereby inhibited from rotating or rolling into a position wherein they may be removed from a seated configuration. The elongated throughbores 423, 424 further inhibit the pivot bases 50 from rolling out of the seated or retained configuration when a bone screw 70 is installed within a vertebra 7 and the bone screw head end 72 is seated and reexpanded within the opening 52 of the pivot base 50 and is retained therein by the retention lip 58.

Looking now to FIGS. 30-33, another embodiment according to the present invention is shown in the form of a dynamic bone plate system 510. The dynamic system 510 comprises a bone plate member 520 that is similar in some respects to the plate member 220 from the previously discussed standard or non-dynamized bone plate system 210. For example, the plate member 520 features apertures 532, end impressions 533, and side impressions 534 which are similar to the apertures 232 and impressions 233, 234 featured on the previous bone plate member 220. The bone plate 520 comprises three pairs of throughbores, and in the present system 510 the central pair are standard, non-dynamized throughbores 522 featuring peg slots or cavities 540, as the throughbores 522 are configured to accommodate the generally spherical pivot bases 150 with extended members 160 discussed above. The two pairs of throughbores adjacent to the standard throughbores 522 feature dynamized throughbores 523 configured to accommodate the spherical pivot bases 50 that may pivot within the throughbores 523 about all three primary axes as defined above. In a preferred form, the throughbores 523 allow generally the same lengths of translation as the dynamized throughbores 423 would allow in the dynamic bone plate system 410 described above, which may be approximately 1.25 millimeters for example.

Though the present dynamic bone plate system 510 is shown with only three pairs of throughbores, it will of course be appreciated that other embodiments having two, four, or even five or more sets of throughbores may be possible. As previously described, the throughbores disposed progressively further away from the standard, non-dynamized pair of throughbores 522 would preferably allow progressively greater lengths of translation in the direction generally parallel to the longitudinal axis of the bone plate. In addition, it will be appreciated that for other possible embodiments according to the present invention that are similar to the present dynamic bone plate system 510 but feature more than three pairs of throughbores, the standard, non-dynamized pair of throughbores 522 may feature the pivot bases 150 with extended members or pegs 160 while the dynamized sets of throughbores may feature the spherical pivot bases 50 that do not feature extended members.

The standard throughbores 522 of the system 510 will feature access slots or cavities 540 to accommodate the use of pivot bases 150 comprising extended members 160. The spherical pivot bases 150 will preferably be seated in the same manner described above with respect to the standard bone plate system 110. The extended posts or pegs 160 serve to add to the torsional resistance of the plate member 520 in the region of the stationary vertebra 7 as well as limit the range through which the pivot bases 150 may pivot, as the posts 160 will eventually contact the bone 7 if pivoted far enough and the pivot base 150 is inhibited from rotating about one of the three primary axes. In a dynamized or dynamic throughbore such as the dynamized or elongated throughbores 523, it is not preferable to use a pivot base with extended members such as the pivot base 150 because the extended members 160 could restrict the desired range of motion. In a standard, non-dynamized throughbore 522 of the present dynamic bone plate system 510 however, a pivot base with extended members such as the pivot base 150 may be preferred. In this way, the spherical pivot bases 150 placed in the standard throughbore 522 will resist torsional stress and will not be free to rotate about the central axis of the throughbores 522, but the other spherical pivot bases 50 without extended members 160 that are seated within the elongated throughbores 523 are free to undergo pivotal and translational motion as well and rotate about the central axis of the throughbore 523.

In another aspect of the present invention, the dynamic bone plate systems 410 and 510 may employ a retainer or guide (not shown) during the installation of the bone screw 70 in a dynamized throughbore 423, 424, 523 that would hold the pivot base 50 within the throughbore in a particular orientation and aid the surgeon or clinician in spacing the pivot bases 50 to the farthest removed ends 423*a*, 424*a*, 523*a* from the standard, non-dynamized pair of throughbores 422, 522. A guide or retainer would aid the surgeon in creating optimal spacing between pivot bases 50 and insert the bone anchors 70 while allowing greater control over the bone anchor insertion trajectories so that the bone anchors 70 may be driven into bone 7 in the most desirable insertion angles. According to the needs of the patient and/or the preferences of the surgeon, a plurality of guides (not shown) offering various angles of trajectory or a single guide (not shown) which may be adjustable to any angle within a predetermined range of angles or to any of a predetermined set of available angles may be available.

It will, of course, be appreciated that a monoplate embodiment of a dynamic bone plate system utilizing a number of combinations of features of the previously discussed bone plate systems 310, 410, 510 is possible. It will also be appreciated that many combinations of features from the exemplary embodiments discussed above are possible, and that the invention is meant to encompass these and any other embodiments possible within the true scope and spirit of the appended claims.

The materials to be used for the bone plate systems 10, 110, 210, 310, 410, 510 described above must be sufficiently strong and demonstrate desirable mechanical characteristics while also fulfilling other requirements such as biocompatibility and galvanic corrosion considerations. For example, the bone plate members 20, 120, 220, 320, 420, 520 may be composed at least partially of titanium, a titanium alloy, polyetheretherketone (PEEK), or carbon-fiber PEEK composite. The pivot base members 50, 150 may be composed at least partially of titanium, a titanium alloy, or cobalt-chrome alloy. Bone anchor members such as the bone screws 70 may be composed at least partially of titanium or titanium alloy. It will, of course, be appreciated that the materials listed herein are listed for exemplary purposes only, and the components described above could be composed of any materials that satisfy the mechanical, chemical, galvanic, and biocompatibility considerations necessary for successful implementation of bone plate systems embodying features in accordance with the present invention.

It will further be appreciated that while there have been described herein several particular embodiments of the present invention, the embodiments presented herein are not limiting and are presented herein for exemplary purposes only. Numerous changes and modifications may occur to those skilled in the art, and it is intended that the appended claims cover all those changes and modifications which fall within the true spirit and scope of the present invention. The present invention shall therefore be recognized to include any and all embodiments that fall within the scope of the appended claims.

What is claimed is:

1. A bone plate system comprising:
an elongate plate member having upper and lower surfaces;
a plurality of throughbores of the plate member;
a plurality of bone anchor members for extending through the throughbore and being driven into bone;
a resilient head portion of at least one of the bone anchor members;
at least one substantially rigid retainer base member for being received in one of the throughbores;
cooperating surfaces of the retainer base member and the one throughbore configured for allowing relative shifting therebetween;
a through opening of the substantially rigid retainer base member sized and configured so that compression of the resilient head portion with an insertion tool allows the resilient head portion to be seated in the opening of the rigid retainer base member, with the rigid base member keeping the seated head portion from backing out therefrom, the retainer base member allowing relative shifting between the bone plate member and the one bone anchor member driven into bone with the resilient head portion seated in the retainer base member;
a lip of the plate member extending about the one throughbore and defining a narrow portion thereof adjacent the lower surface of the plate member with the lip configured to be in interference with the retainer base member and limit shifting of the retainer base member toward the lower surface of the plate member;
a rigid body of the retainer base member extending about the through opening thereof that is configured such that the rigid body resists deformation of the retainer base member with seating of the resilient head portion of the bone anchor member in the through opening of the retainer base member; and
at least one access slot in communication with the one throughbore to permit the retainer base member to be inserted therein for receipt of the one bone anchor member extending through the through opening thereof.

2. The bone plate system of claim 1 wherein the base member through opening has an entry diameter, and the resilient head portion has a maximum diameter that is larger than the entry diameter.

3. The bone plate system of claim 1 wherein the retainer base member includes a radially inward extending portion that is sized to be in interference with the resilient head portion.

4. The bone plate system of claim 1 wherein the base member has a radially extending pivot portion received in the access slot so that the base member pivots about the pivot portion and the pivot portion limits rotation of the base member in the one through bore.

5. The bone plate system of claim 1 wherein the resilient head portion has flanges extending therefrom for being engaged by an insertion tool to compress the head portion.

6. The bone plate system of claim 1 wherein the resilient head portion is configured to be radially compressible.

7. A bone plate system comprising:
an elongate plate member having upper and lower surfaces;
a plurality of throughbores of the plate member each extending along a respective bore axis between the upper and lower surfaces of the plate member;
a plurality of bone anchor members for extending through the throughbores;
head portions of the bone anchor members for being engaged by a tool to drive the bone anchor members into spinal bones;
at least one rigid retainer base member for being received in one of the throughbores and having an opening configured to receive one of the bone anchor members extending therethrough with the head portion of the one bone anchor member seated therein;
cooperating rigid surfaces of the rigid retainer base member and the one throughbore configured for allowing relative shifting therebetween with the one bone anchor member driven into a bone and the head end thereof seated in the rigid retainer base member opening;
a rigid retention portion of the rigid retainer base member sized to keep the one bone anchor member head end seated in the opening of the rigid retainer base member against backing out therefrom;
the cooperating rigid surfaces of the rigid retainer base member and the one throughbore include mating arcuate surfaces of the one throughbore and the rigid retainer base member each having a varying diameter along the bore axis with the arcuate surface of the one throughbore including a minimum diameter thereof and the arcuate surface of the rigid retainer base member including a maximum diameter thereof that is larger than the minimum diameter of the throughbore arcuate surface so as to be in interference therewith to keep the rigid retainer base member in the one throughbore; and an access slot in communication with the one throughbore that permits the rigid retainer base member to be inserted into the one throughbore.

8. The spinal bone plate system of claim 7 wherein the rigid retention portion comprises an overhang portion of the rigid retainer base member that extends radially inward in the opening of the rigid retainer base member.

9. The spinal bone plate system of claim 7 wherein the rigid retainer base member arcuate surface is convex and the throughbore arcuate surface is concave.

10. The bone plate system of claim 7 wherein at least one of the plurality of throughbores is an elongate throughbore, the cooperating surfaces of the rigid retainer base member and the throughbore allowing both pivoting and translation of the base member relative to the plate member within the elongate throughbore.

11. The bone plate system of claim 10 wherein the plate member has at least one retention lip portion extending into the elongate throughbore and sized to retain the rigid retainer base member therein.

12. A bone plate system comprising:
an elongate bone plate member having upper and lower surfaces;
a plurality of throughbores in the plate member, the throughbores extending between the upper and lower surfaces of the bone plate member;
a plurality of bone anchor members for extending through the throughbores and being driven into bone, each of the bone anchor members having a head portion for driving the bone anchor member into bone;
at least one base member for being received in one of the throughbores;
a through opening of the base member arranged to receive one of the bone anchor members extending therethrough and the head portion of the one bone anchor member seated therein;
a pair of access slots of the bone plate member that open to the upper surface thereof and are in communication with the one throughbore which allows the base member to be inserted into the one throughbore for receipt of the one bone anchor member extending therethrough and through the through opening of the base member;
upper rim portions of the plate member extending between the pair of access slots along opposite sides of the one throughbore that are configured to retain the base member in the one throughbore; and
a rigid body of the base member extending about the through opening thereof which does not deform with seating of the head portion of the one bone anchor member in the through opening of the base member.

13. The bone plate system of claim 12 wherein the pair of access slots are diametrically opposed across the one throughbore.

14. The bone plate system of claim 13 wherein the base member has opposed wall portions sized to be fit into the access slots in one orientation and then shifted to another orientation to reorient the base member so that the through opening thereof is generally aligned with the one throughbore for receiving the one bone anchor member therethrough.

15. The bone plate system of claim 12 wherein the upper rim portions have a diameter thereacross, the base member is substantially rigid and has an annular configuration with a maximum diameter larger than the diameter of the upper rim portions, and the pair of access slots comprises a pair of diametrically opposed access slots sized to allow the annular base member to be fit therein.

16. The bone plate system of claim 12 wherein the pair of slots provide the rigid body with clearance for fitting in the throughbore.

17. The bone plate system of claim 12 wherein the plate member has a predetermined thickness, the base member has a generally spherical outer surface, the throughbore has a generally spherical inner surface, and the pair of access slots have a length extending into the throughbore for less than the thickness of the plate member.

18. The bone plate system of claim 12 wherein the plate member has a predetermined thickness, the base member has a generally spherical outer surface, the throughbore has a generally spherical inner surface, and the pair of access slots extend through the thickness of the plate member.

19. A bone plate system comprising:
an elongate plate member;
a plurality of throughbores of the plate member each having a central axis extending therethrough;
a plurality of bone anchor members each having a head end for driving the bone anchor member into bone;
at least one substantially rigid base member configured to be received within one of the plurality of throughbores, the base member having an opening therethrough, and the head end able to be seated within the opening of the base member;
arcuate mating surfaces of the base member and the throughbore configured to allow the base member and associated bone anchor member to substantially freely pivot within the throughbore about the central axis of the throughbore and two mutually orthogonal axes orthogonal to the central axis of the throughbore with the one bone anchor member driven in to bone and the head end thereof seated in the base member opening;
a rigid wall of the base member extending about the opening thereof which does not deform with seating of the head end of the one bone anchor member in the base member opening; and
an access slot in communication with the throughbore that permits the base member to be inserted into the throughbore.

20. The bone plate system of claim 19 wherein at least one of the plurality of throughbores is an elongate throughbore allowing both pivoting and translation of the base member relative to the plate member within the throughbore.

21. The bone plate system of claim 20 wherein the plate member has at least one retention lip portion extending into the elongate throughbore and sized to retain the base member therein.

22. The bone plate system of claim 19 wherein the elongate plate member has a narrow width, and the plurality of throughbores is aligned as a single row of throughbores in the narrow width plate member, each throughbore configured to allow a bone anchor member to pass therethrough into a corresponding vertebral bone.

23. A bone plate system comprising:
a substantially rigid plate member;
a plurality of throughbores of the plate member;
at least one cavity in communication with one of the throughbores;
opposing, straight side walls of the cavity extending from the throughbore;
a plurality of bone anchor members each having a head portion for driving the bone anchor members into bone;

at least one substantially rigid base member configured to be received within the one throughbore and having an opening therethrough, the head portion of the bone anchor member configured to be seated within the opening of the base member;

cooperating surfaces of the base member and the throughbore configured to allow pivoting of the base member within the throughbore relative to the plate member;

at least one pivot member extending from the base member into the cavity disposed between the opposing walls thereof to restrict rotation of the base member in the one throughbore and provide torsional resistance about an axis of the one bone anchor member with the cooperating surfaces allowing pivoting of the base member about a pivot axis of the pivot member and an axis orthogonal to the pivot axis and the bone anchor member axis;

an end wall of the cavity extending between the opposing straight side walls;

an end portion of the pivot member disposed between the opposing straight side walls of the cavity and spaced from the end wall thereof to allow the end portion of the pivot member to move generally parallel to the opposing straight side walls and permit pivoting of the base member about the axis orthogonal to the pivot axis and the bone anchor member axis; and a rigid body of the base member extending about the opening thereof configured so that seating of the head portion of the bone anchor member does not deform the body of the base member and the base member can pivot about both the pivot axis of the pivot member and the axis orthogonal to the pivot axis and the bone anchor member axis with the head portion of the bone anchor member seated in the base member opening.

24. The bone plate system of claim 23 wherein pivoting of the base member about the pivot axis is guided by the opposing walls of the cavity and limited by the pivot member contacting bone.

25. The bone plate system of claim 23 wherein the pivot member comprises a pair of opposite, radially extending pivot members integral with the base member.

26. The bone plate system of claim 23 wherein the plate member has a predetermined thickness, and the cavity extends through the thickness of the plate member.

27. The bone plate system of claim 23 wherein the plate member has a narrow width, and a plurality of throughbores is aligned as a single row of throughbores in the narrow width plate member, each throughbore configured to allow a bone anchor member to pass therethrough into a corresponding vertebral bone.

28. A bone plate system comprising:
an elongate plate member having an elongate axis thereof;
a plurality of throughbores of the plate member;
a plurality of bone anchor members each having a head end for driving the bone anchor members into spinal bones;
at least one base member for being received in one of the throughbores and having an opening therethrough configured to receive one of the bone anchor members extending therethrough with the head end of the bone anchor member seated within the opening thereof;
at least one pivot member extending between the base member and the plate member;
an access slot extending radially from the one throughbore in an axial direction along the plate member for receiving the pivot member therein to allow pivoting of the base member in the one throughbore about the pivot member;

a lip of the plate member extending about the one throughbore and defining a narrow portion thereof with the lip configured to be in interference with the base member and limit pivoting of the base member in the one throughbore beyond the lip; and a rigid continuous wall of the base member extending completely around the opening thereof without interruption and which extends between the head end of the bone anchor member and the plate member to completely space the head end from the plate member with the head end seated in the opening of the base member.

29. The bone plate system of claim 28 wherein the access slot has opposing walls and is in alignment with the elongate axis of the plate member, and the opposing walls are configured to guide pivoting of the base member about the pivot member with the pivot member disposed therebetween.

30. The bone plate system of claim 28 wherein the access slot has opposing walls, and the pivot member provides torsional resistance of the base member to rotation within the throughbore with the pivot member received between the opposing walls of the access slot.

31. A bone plate system comprising:
an elongate plate member extending along an axis thereof, the plate member having upper and lower surfaces;
a plurality of throughbores of the plate member, each throughbore extending along a respective bore axis between the upper and lower surfaces of the plate member;
a plurality of access slots adjoining at least one throughbore of the plate member, the access slots each having a pair of confronting walls extending away from the throughbore;
at least one base member having projecting members extending therefrom, the base member configured to be received within the throughbore and each projecting member configured to be received within one of the corresponding access slots, the access slots inhibiting rotation of the base member about the bore axis;
an upper portion of the throughbore that opens to the upper surface of the plate member and is in communication with the access slots to allow the base member to be inserted downwardly into the upper portion of the one throughbore with the projecting members advancing downwardly into the access slots between the confronting walls thereof; and
a substantially rigid body of the base member having an opening sized to receive a bone anchor extending therethrough with the rigid body configured to resist deformation of the base member with seating of a head end of the bone anchor member in the opening of the rigid body.

32. The bone plate system of claim 31 wherein the throughbores are arranged as a single row of throughbores in substantial alignment with the elongate axis of the plate member.

33. The bone plate system of claim 31 wherein the confronting walls extending from the throughbore extend substantially along the elongate axis of the plate member.

34. The bone plate system of claim 31 wherein the access slots of the plate member terminate with a curved wall portion and the projecting members of the base member terminate in a generally curved surface, the curved wall portion configured to avoid interference between the generally curved surface of the projecting members and the curved wall portion of the access slots as the base member pivots relative to the plate member.

* * * * *